US010952751B2

(12) United States Patent
Brown

(10) Patent No.: US 10,952,751 B2
(45) Date of Patent: Mar. 23, 2021

(54) SURGICAL TARGETING SYSTEMS AND METHODS

(71) Applicant: Roy Anthony Brown, San Diego, CA (US)

(72) Inventor: Roy Anthony Brown, San Diego, CA (US)

(73) Assignee: MARKSMAN TARGETING, INC., San Diego, CA (US)

(*) Notice: Subject to any disclaimer, the term of this patent is extended or adjusted under 35 U.S.C. 154(b) by 451 days.

(21) Appl. No.: 15/330,875

(22) Filed: Nov. 9, 2016

(65) Prior Publication Data
US 2017/0296202 A1  Oct. 19, 2017

Related U.S. Application Data

(63) Continuation-in-part of application No. 14/659,497, filed on Mar. 16, 2015, now abandoned.

(60) Provisional application No. 61/954,250, filed on Mar. 17, 2014.

(51) Int. Cl.
| | |
|---|---|
| *A61B 90/11* | (2016.01) |
| *A61B 17/17* | (2006.01) |
| *A61B 34/20* | (2016.01) |
| *A61B 90/00* | (2016.01) |
| *A61B 34/10* | (2016.01) |
| *A61B 17/34* | (2006.01) |
| *A61B 90/13* | (2016.01) |
| *A61B 6/02* | (2006.01) |
| *A61B 90/30* | (2016.01) |

(52) U.S. Cl.
CPC ...... *A61B 17/1703* (2013.01); *A61B 17/3472* (2013.01); *A61B 34/10* (2016.02); *A61B 34/20* (2016.02); *A61B 90/11* (2016.02); *A61B 90/13* (2016.02); *A61B 90/37* (2016.02); *A61B 90/39* (2016.02); *A61B 6/02* (2013.01); *A61B 90/30* (2016.02); *A61B 2034/107* (2016.02); *A61B 2034/2051* (2016.02); *A61B 2034/2057* (2016.02); *A61B 2090/067* (2016.02); *A61B 2090/068* (2016.02); *A61B 2090/367* (2016.02); *A61B 2090/374* (2016.02); *A61B 2090/376* (2016.02); *A61B 2090/3764* (2016.02); *A61B 2090/3966* (2016.02); *A61B 2090/3975* (2016.02); *A61B 2090/3983* (2016.02)

(58) Field of Classification Search
CPC . A61B 17/17; A61B 17/1703; A61B 17/1739; A61B 17/1742; A61B 17/1746; A61B 17/1757; A61B 90/06; A61B 90/14
USPC .................................. 606/96, 102; 600/587
See application file for complete search history.

(56) References Cited

U.S. PATENT DOCUMENTS

| | | | |
|---|---|---|---|
| 5,891,158 A * | 4/1999 | Manwaring | A61B 90/14 600/102 |
| 2011/0060339 A1* | 3/2011 | de Wekker | A61B 5/1071 606/80 |

* cited by examiner

*Primary Examiner* — Si Ming Ku
(74) *Attorney, Agent, or Firm* — Coastal Patent Law Group, P.C.

(57) ABSTRACT

A medical device having a body having a first bubble vane for measuring angle in one plane; said body having a second bubble vane for measuring an angle in another plane; said first bubble vane having angle indicia; said second bubble vane having angle indicia; said one plane being the in a different plane from said another plane and the angles in the two planes providing the entry point for an incision for the placement of an orthopedic device.

3 Claims, 23 Drawing Sheets

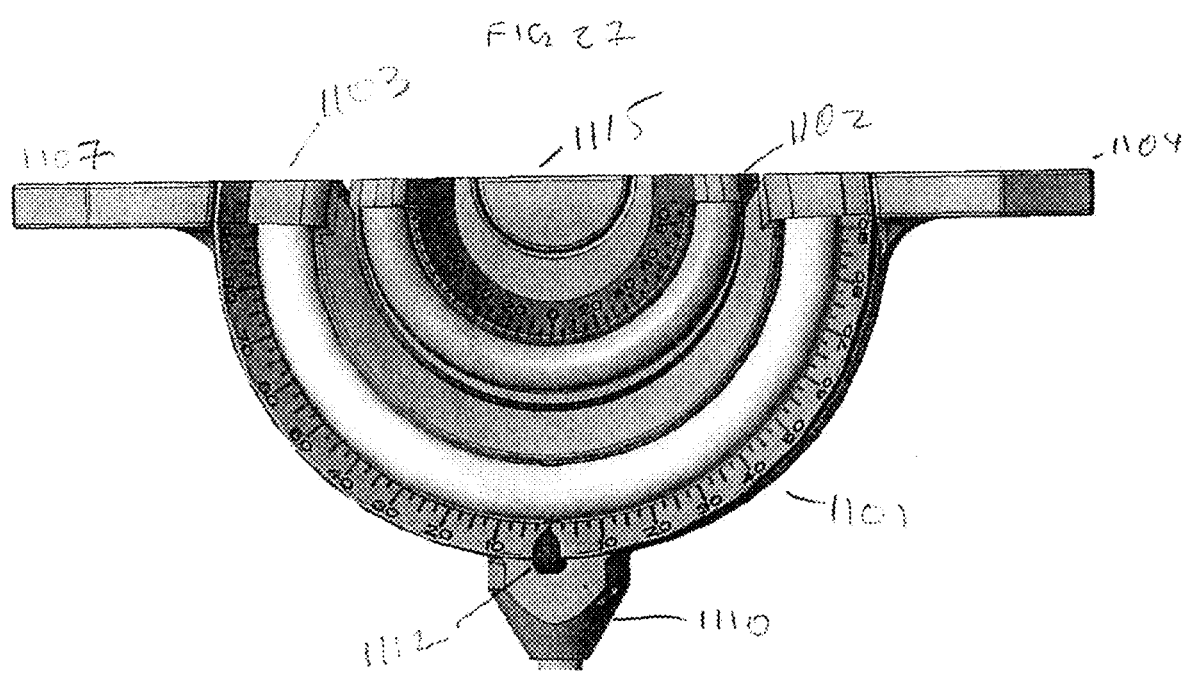

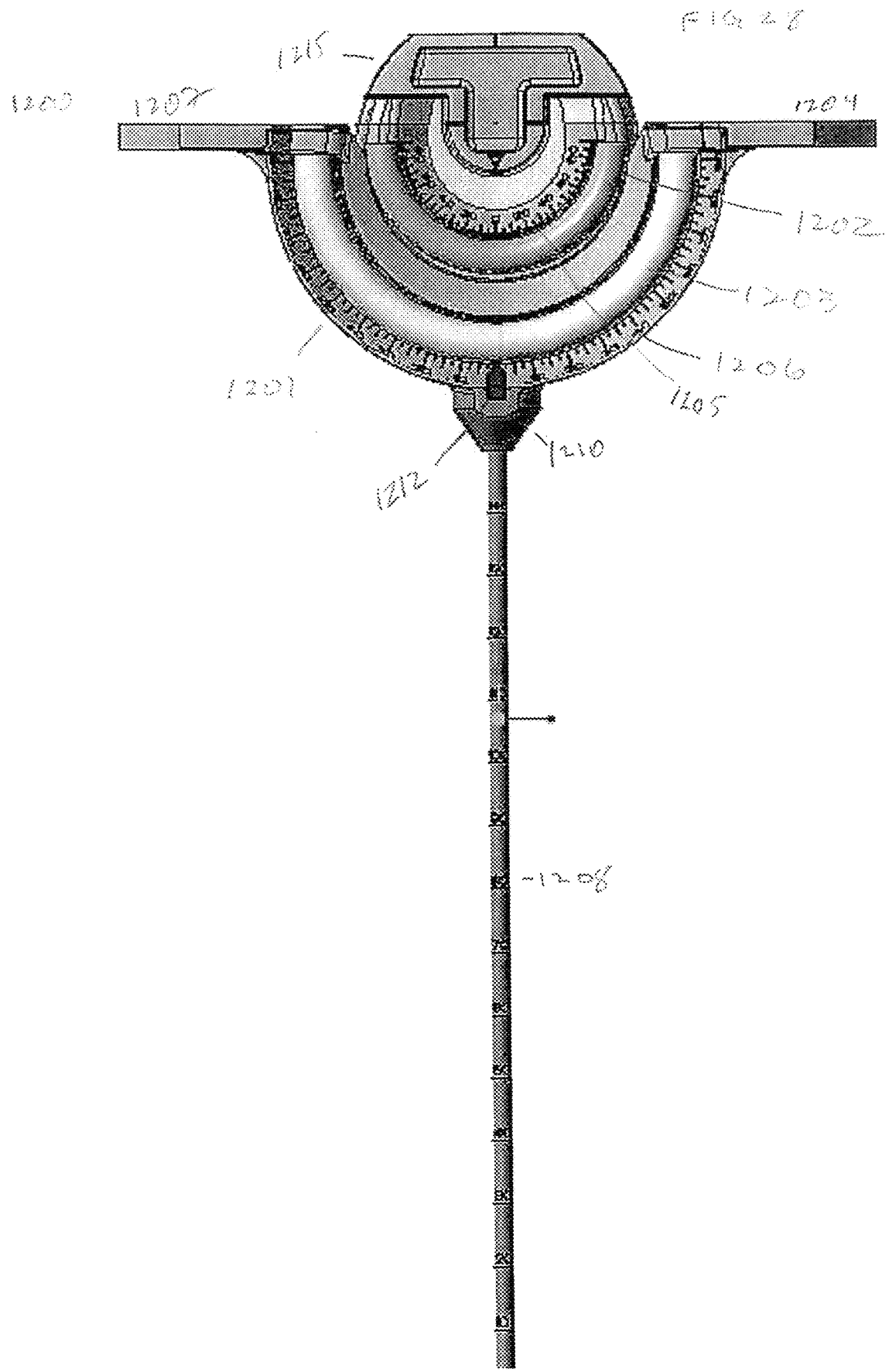

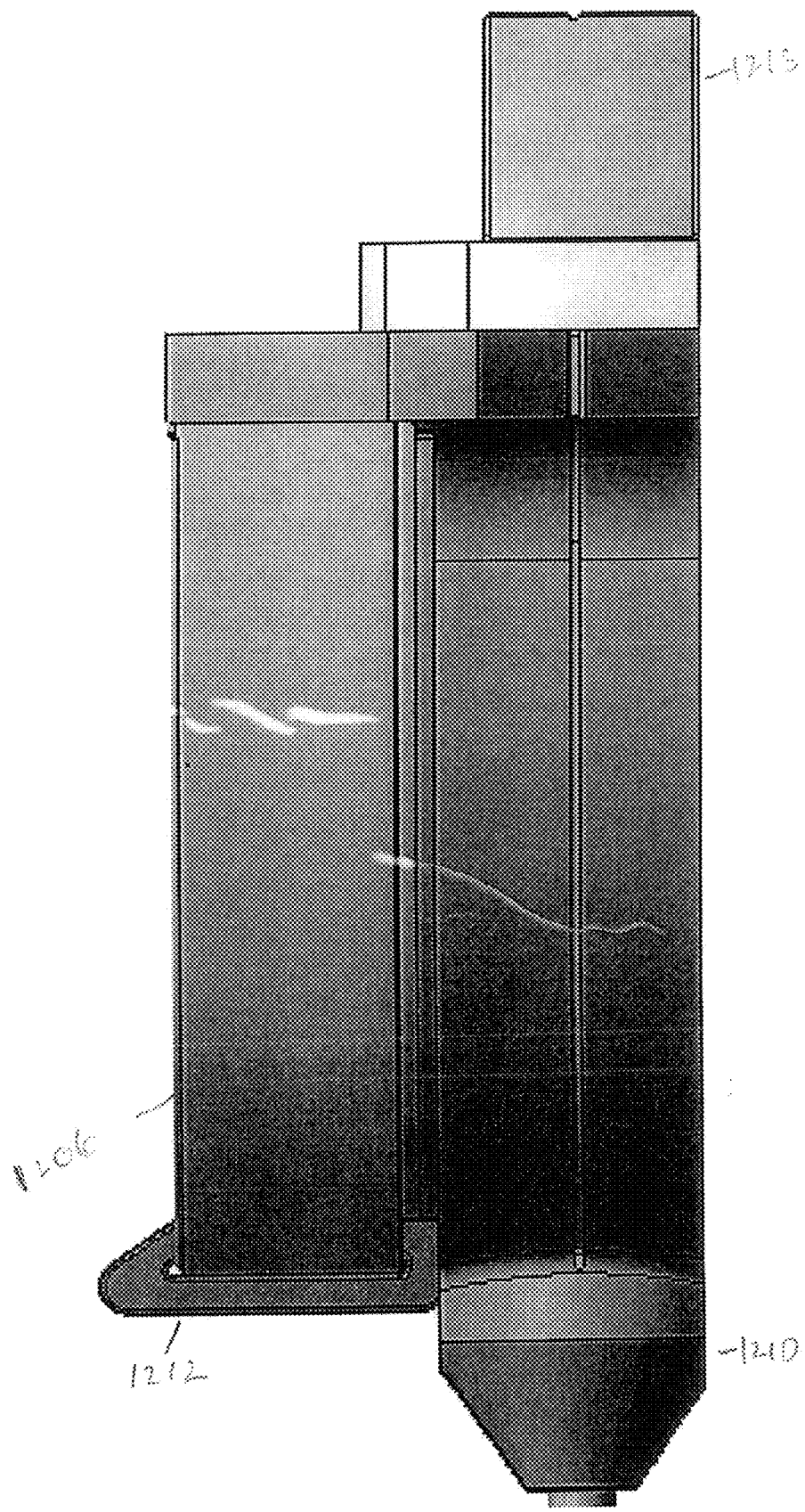

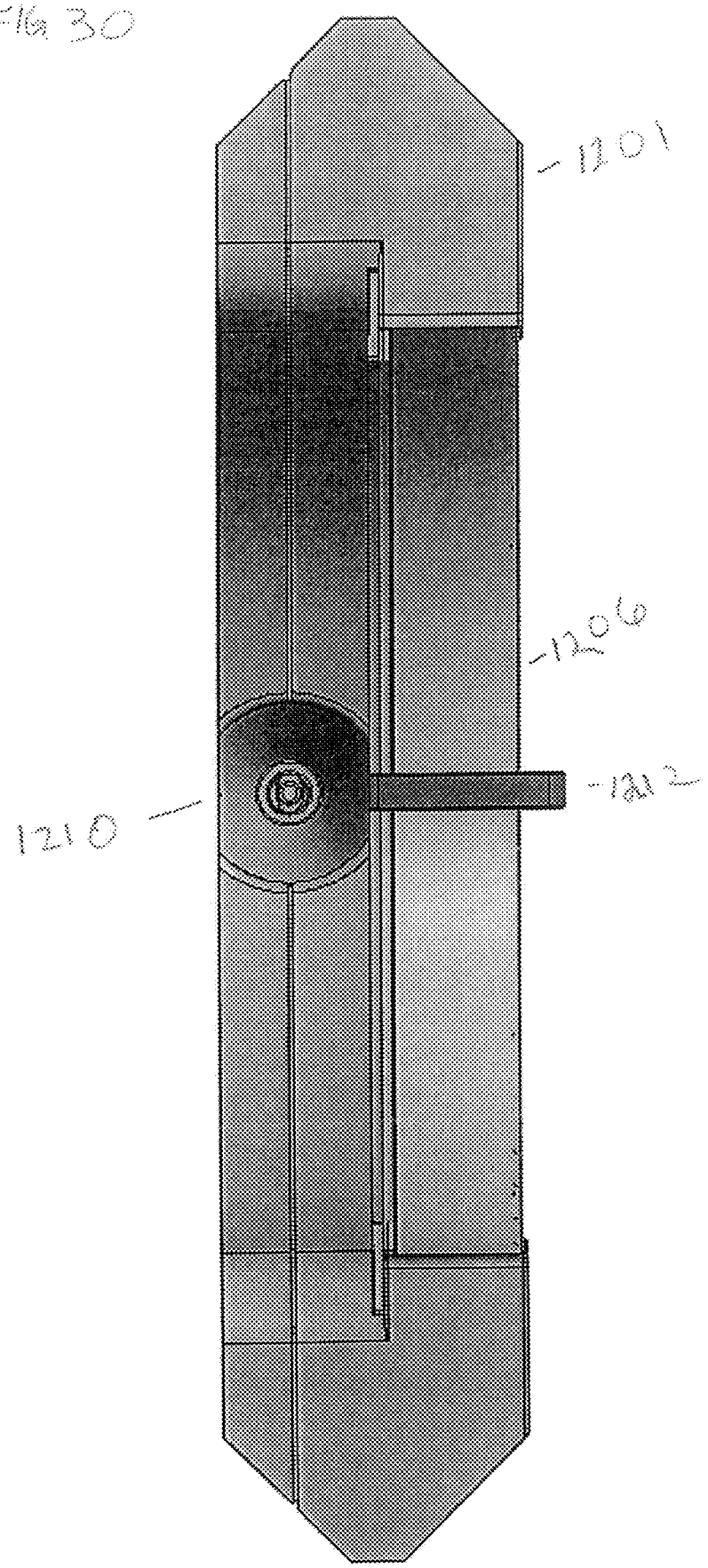

SURGICAL TARGETING SYSTEMS AND METHODS

CROSS REFERENCE TO RELATED APPLICATIONS

This application is a continuation in part (CIP) of commonly owned U.S. Ser. No. 14/659,497, filed Mar. 16, 2015; which further claims benefit of U.S. Provisional Ser. No. 61/954,250, filed Mar. 17, 2014.

BACKGROUND

Field of the Invention

The present invention relates to a system and method to aid the placement of surgical devices under radiographic image guidance. More particularly, embodiments of the invention relate to a system utilizing radiopaque markers, an external light source and targets. Light is projected onto the skin or surgical site over a target in conjunction with a radiographic line marker superimposed on a fluoroscopic image to identify bone landmarks and angles so that skin entry points can be identified. This can be augmented by the use of a target system that is held in place by a bedside rail mounted mechanical arm that can hold any position desired. This allows rigid guidance of guide wire to facilitate the accurate placement of surgical implant or devices. An exemplary system utilizes a radiopaque marker, external laser markers and a target to determine intraoperative angles, trajectories and positioning coordinates to facilitate placement of needles, guide wires, trocars and cannulae for the surgical placement of orthopedic implantation devices.

Description of the Related Art

Many fluoroscopy systems, whether analog or digital, on the market possess a laser "aimer" or pointer that is used in conjunction with the imaging source. One example is the Smart Laser Aimer from GE OEC (GE Healthcare, Salt Lake City, Utah). The laser pointer is mounted on the Image Intensifier of the C-arm and is used as a line of sight pointer. The laser light illuminates the center point on the surgical site where the x-ray beam will image if activated, giving the user a more accurate location of the image. It does not accurately place the image in global 3-dimensional space, nor does it provide an accurate location with respect to anatomical landmarks. The user must rely on more complex image guidance systems intraoperatively, or 3-D image reconstruction software preoperatively in order to obtain more accurate information for precise instrument placement. One example of intraoperative guidance systems is the StealthStation from Medtronic. Such systems require a dedicated piece of equipment to transmit and receive signals and markers on the surgical instruments to track the position and orientation of each instrument. Dedicated software and image storage are also required to incorporate guidance system information into preoperative or intraoperative images. Such systems do not have the benefit of the present invention of being compatible with any commercially available imaging equipment and surgical instruments.

There are many targeting or aiming apparatus for making bores in bones as described in U.S. Pat. No. 50,312,013 which utilizes a laser and a fixed target in combination with x-rays. More recently, there have been articles focusing on targeting with a complex computer aided technique such as, "Percutaneous Lumbar Pedicle Screw Placement Aided by Computer-Assisted Fluoroscopy-based Navigation" by Benson P. Yang, MD, Melvin Wahl, MD, CARY S. Idler MD, Spine:37(24):2055-2060. There have also been other publications such as, "Accuracy of Fluoroscopically assisted laser targeting of the cadaveric thoracic and lumbar spine to place transpedicular screws" by Schwend, R M, Dewire P J, Kowalski T M; J Spinal Disord. 2000 October; 13 (5): 412-8; "Pedicle Guide for Thoracic Pedicle Screw Placement" by Kingsley O. Abode-Iyamah MD; Luke Stemper BS; Shane Rachman BS; Kelly Schneider BS; Kathryn Sick BS Patrick W. Hilton MD, University of Iowa Hospitals and Clinics; and the work of C. Grady McBride at the Orlando Orthopaedic Center, where reduction of fluoroscope times resulted in the use of a targeting device in parallel for insertion of a guide wire.

The fluoroscopy systems operate on either a continuous or pulsing system for x-rays to permit continuous or near continuous monitoring of the medical procedure involved. In either situation there is still a need to reduce or limit the exposure of patients to the exposure of the x-ray radiation. Timing is critical, but in the surgeries utilizing today's fluoroscopy systems there is somewhat a hit and miss approach to finding the landmarks need for the attachment of screws for spinal surgery, as the procedure follows a general methodology of measurement and a grid pattern that often does not consider the thickness of a patient's soft tissue and muscle from the area of attachment, such as the pedicles of the spine. The use of Jamshidi needles, trocars and cannulae for certain surgeries help limit wound size and openings, but the degree of precision desired is still not met using the current methods, even with complex software and robotics. The degree of precision has greatly improved, but the accuracy of the puncture for attaching screws in the body still relies on an estimate of the location of the incision without an exemplar or marker to follow or a more accurate place in which to make the incision. For example, in spine surgery the standardized methodology will be to measure from the midline to a fixed distance to make an incision with limited regard to the angle of entry and if the landmark is not hit on the first attempt there are continued attempts and the need for dealing with tissue and muscle as the trocar or cannula is being positioned to find the pedicle landmark. This increases unnecessary exposure to x-rays and the increased chance of injury to tissue and muscle.

Also, the focus is minimally invasive surgery is to limit the need for opening the body and increase the risk of infection and healing. In the use of robotics, for instance, section of the spine still need to be exposed to attach the rail for the robotic system to be used during spine surgery. While this may be an improvement over opening the entire area of the spine, it still creates issues around infection and healing of the wounds. While the methodologies used to get towards minimally invasive surgery have improved there is significant opportunity for an increase in accuracy to go along with the increase in precision.

SUMMARY OF THE INVENTION

The present invention is a system and method used in conjunction with fluoroscopic imaging systems to identify bone landmarks and angles, skin entry points and trajectories and a target guide holder in order to aid the placement of surgical instruments, such as guide pins, needles, trocars, fixation hardware and cannulae. The system's utility is not limited to a particular anatomical location, and thus can be used in a wide range of variety of surgical applications. In addition to the spine surgery application detailed below, it can be used in human, veterinary, or training models for cranial, hip, knee, and wrist surgery, for example.

The system comprises an adjustable radiopaque bar marker mounted below external light sources, such as visible light sources or lasers, the associated mounting hardware on the imaging system and a separate targeting guide holder. The mounting hardware allows the radiopaque marker to translate around and across the circumference and face 360° around the image intensifier. The radiopaque bar is able to rotate 90° along the axis parallel to the image intensifier allowing the marker to be effectively radiolucent. Additionally, the radiopaque marker is centered on the intensifier which eliminates the issue of beam divergence. The system is used in conjunction with commonly available preoperative images and commercially available intraoperative radiography equipment. A preoperative image of the intended surgical site is taken using computed tomography (CT) or magnetic resonance Imaging (MRI). It should be noted that the image is already taken to judge the surgical candidacy.

On this image, the anatomy of the intended surgical site is seen and used to preoperatively plan the angles, trajectories and positioning of the surgical instruments by superimposing points and lines on the preoperative image. From this preoperative plan, the intended lateral line and transverse line on the skin and the anterior/posterior (AP) angulation of each instrument is planned. There are three methods contemplated for acquiring the lateral line: (1) use the angle found from the pre/intra operative CT/MRI and position the C-arm to that angle and line up the radiopaque marker over the pedicle; (2) measure the distance from the midline to exit point on the skin; and (3) landmark of the plumb line from exit point of the skin when drawing angles. This crossing of lines identifies true coordinate for entry point. Once the lateral line and the transverse line are established, the Jamclometer tip is placed on the intersection point. Using a two-axis inclinometer the AP angle can be applied in the x plane. While in the lateral plane, the Y angle can be found from the indicator on the C-arm or it can be found by lining up the marker on top of the Jamclometer with the laser and using the angle off of the Jamclometer. Further, the top midline of the Jamclometer can be aligned with the light line and the y angle can be read off the inclinometer. The preoperative planning step may be performed manually on a printed image or electronically using commercially available software and a digital image. Additional lines are constructed on the preoperative image by projecting the position of the intended entry points on the skin in the orthogonal planes to be used for intraoperative imaging at the time of surgery. The intersection of the orthogonal projection lines with anatomical landmarks indicates which anatomical landmark to use in intraoperative imaging to align the system. intraoperative planning may also be performed in the same manner using intraoperative images.

Prior to the procedure, the light source is mounted to a commercially available radiographic imaging system, such as a fluoroscope or portable x-ray. The light beams are projected as a line onto the skin at the surgical site. The radiopaque bar markers and light sources are located in known positions with respect to the imaging system. The radiopaque bar markers are imaged with the anatomical location of interest, and the light sources are projected onto the skin in the plane of the intended entry point determined in pre- or intraoperative planning. The intersection of two linear light beams in orthogonal planes, typically but not necessarily the anterior/posterior (AP) and medial/lateral (ML) planes, clearly mark the entry point of the surgical instruments on the skin of the patient. The orientation of the surgical instruments at the entry point is set using the target guide holder, an angularly adjustable, bi-planar, mechanical guide to set the angle of the instruments in both orthogonal planes per the pre- or intraoperative plan. The system thereby provides accurate both the positioning coordinates and the orientation of the surgical instrument to the surgeon, such that if the resulting trajectory is followed, the instrument will reach the intended internal surgical site without direct visualization by dissection or repeated radiographic exposures.

An example of the method using the present invention and a preoperative plan includes an axial preoperative image, also known as a "slice", of the intended surgical site is taken using computed tomography (CT) or magnetic resonance imaging (MRI). On this image, the anatomy of the intended surgical site is seen in cross-sectional axial view (a view not commonly available intraoperatively) and used to preoperatively plan the angles, trajectories and landmark positioning of the surgical instruments. From this preoperative plan, the intended skin entry point is defined for the AP plane. An example of the method using the present invention and an intraoperative plan includes a lateral intraoperative image using fluoroscopy or portable x-ray. On this image, the anatomy of the intended surgical site is seen in side elevation and used to plan the angles, trajectories and positioning of the surgical instruments. From this intraoperative plan, the intended skin entry and bone entry point is defined in the ML plane. When the two exemplary methods are used together, for example in spinal surgery, the intersection of the AP and ML planes using the light beam mark the surgical skin entry point coordinate. The use of the target guide holder insures no human initiated deviation from plotted trajectory is introduced during insertion. This method and device are ideal for minimally invasive procedures including but not limited to discectomy, pedicle screw placement for fixation, facet fusion, facet joint injection, nerve ablation, vertebral augmentation.

Another example of the method is for training surgeons in using the invention for improved performance and accuracy. The intersection of the AP and ML Planes using the light beam mark the surgical skin entry point and the surgeons get use to understanding the various degrees of entry required, such that in the case of the back surgery of the previous paragraph, the angles become familiar to the surgeon through identification training and they become more accurate in the surgical entry point and the angles of that entry point. Clearly, the invention is applicable for use with not only spinal surgery but also orthopedic surgeries involving shoulder, hips, joints, wrist, arms, legs, ankles hands and feet.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 27 illustrates the Spotter Body ready to receive a needle, cannula, pin or start wrench at connector or any similar such device for use during orthopedic surgery.

FIG. 28 illustrates an alternative Spotter.

FIG. 29 shows a side view of the Spotter.

FIG. 30 illustrates a bottom view of both Spotter.

DETAILED DESCRIPTION OF THE PREFERRED EMBODIMENTS

Figure 1:
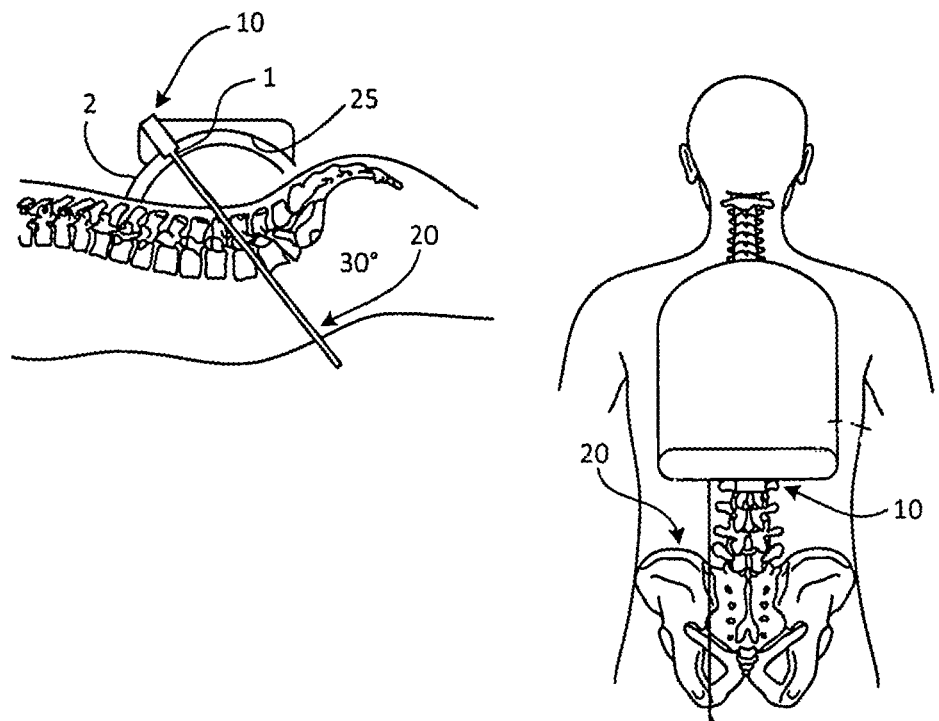
FIG. 1 is a translucent illustration of the lateral and posterior views of the surgical patient, with the linear light beam externally positioned in the posterior view and the intended trajectory of a surgical instrument through the body in the lateral view.

First, the light source 1 in FIG. 1A must be positioned. A collar system 2 will fit the image intensifier 10 incorporating the light source 1 and the radiopaque marker 25. As shown in FIG. 1A and FIG. 1B, using the radiopaque marker 25 on the face of the laterally positioned image intensifier 10 fluoroscopically the light source trajectory 20 is determined through the spine segment. By superimposing the marker over the anatomy, the system automatically places the laser marker over the skin as shown at 30. This determines both the angle and latitude position on the skin to start the procedure.

Figure 2:
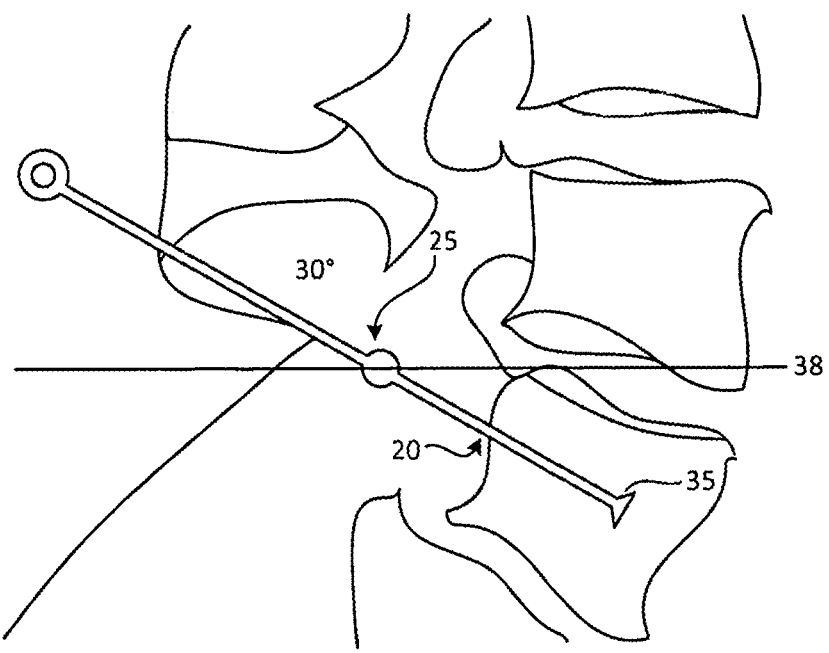
FIG. 2 is an example of the instrument trajectory of FIG. 1A as projected on a radiographic image.
Figure 3:
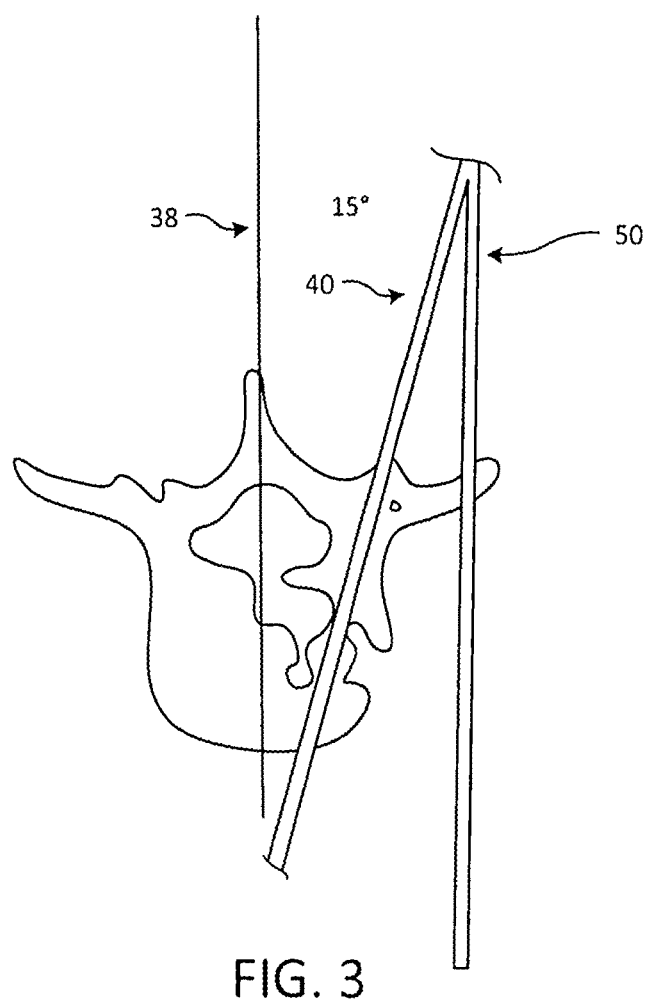
FIG. 3 is an illustration of the determination of the surgical angle and projection of the entry point of the skin on an anatomical landmark on a preoperative CT image.
Figure 4:
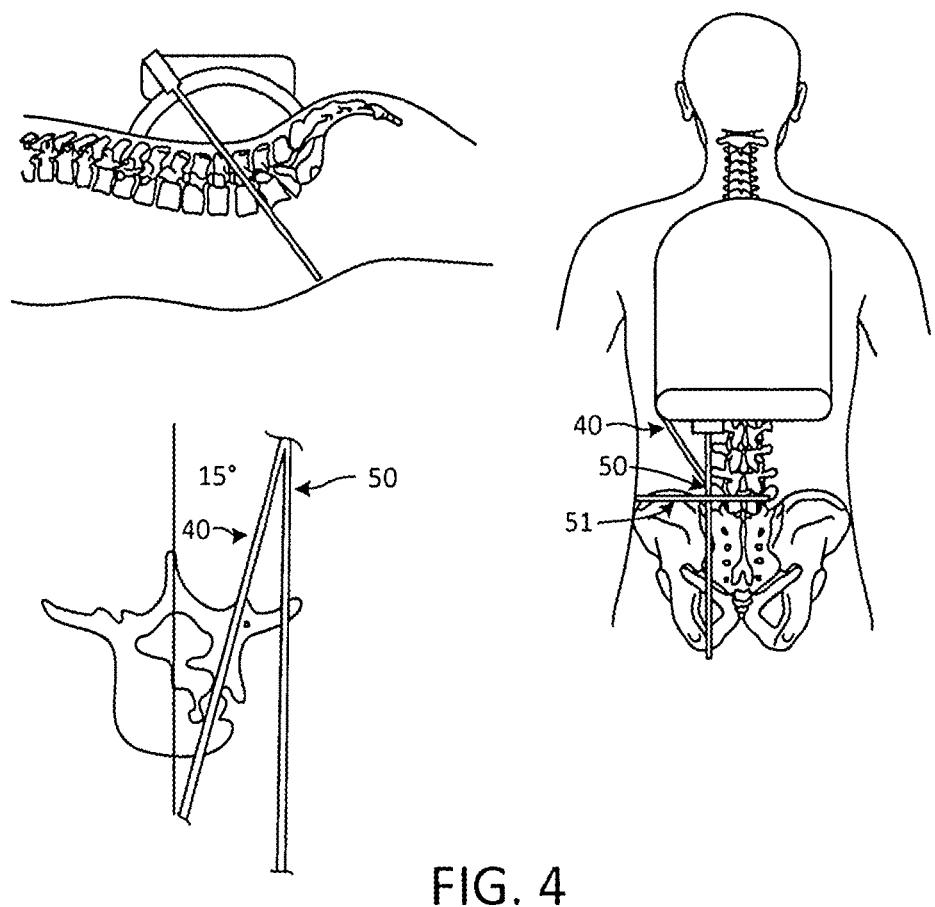
FIG. 4 is an illustration of completing the A/P positioning technique by locating the anatomical landmark.
Figure 5:
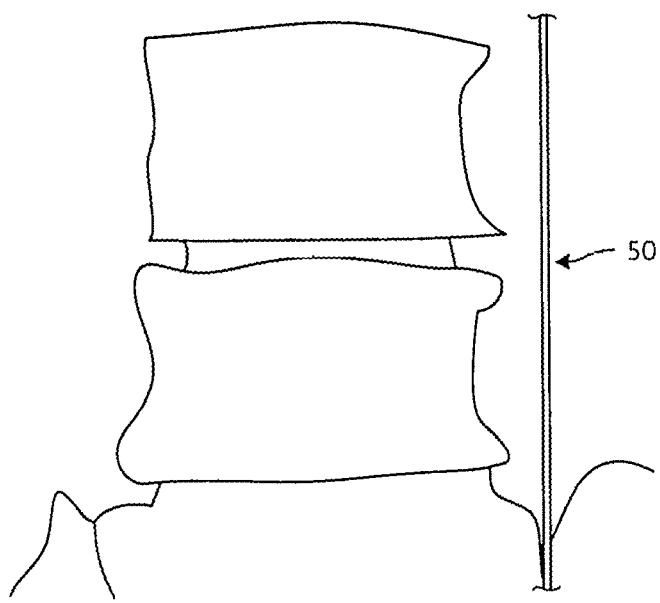
FIG. 5 is radiograph example of the technique of FIG. 5.
Figure 6:
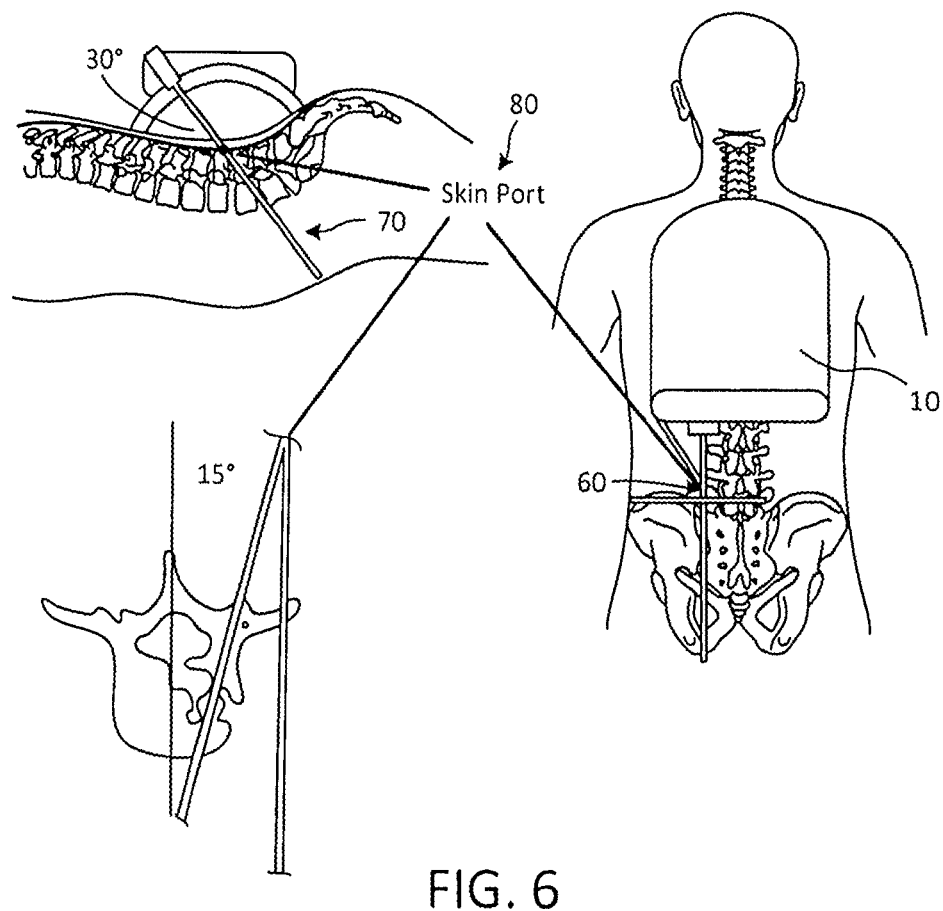
FIG. 6 is an illustration of the guide pin insertion.

Next, the A/P position must be determined by looking at the preoperative axial view of the target in question. In FIG. 2, the target in question is a vertebral body 35. The midline 38 is determined, an azimuth through the pedicle or structures desired is positioned, and an angle is determined that would effectively produce the correct trajectory 40 through the anatomy. For example, FIG. 3 illustrates an angle of 15 degrees at the feature of interest, the end of transverse process. The A/P landmark is determined by using the axial view (FIG. 4) by looking down through the anatomy from the point in which the azimuth exits the body posteriorly 40. FIG. 4 illustrates the example of the trajectory overlying the end of the transverse process 50. The intersection of 50 and 40 is shown at 51. Finally, using the radiopaque marker on the face of the A/P intensifier, the marker is fluoroscopically superimposed over the landmark previously identified. In the example shown in FIG. 4, FIG. 5, and FIG. 6 this is the end of the transverse process.

Figure 7:
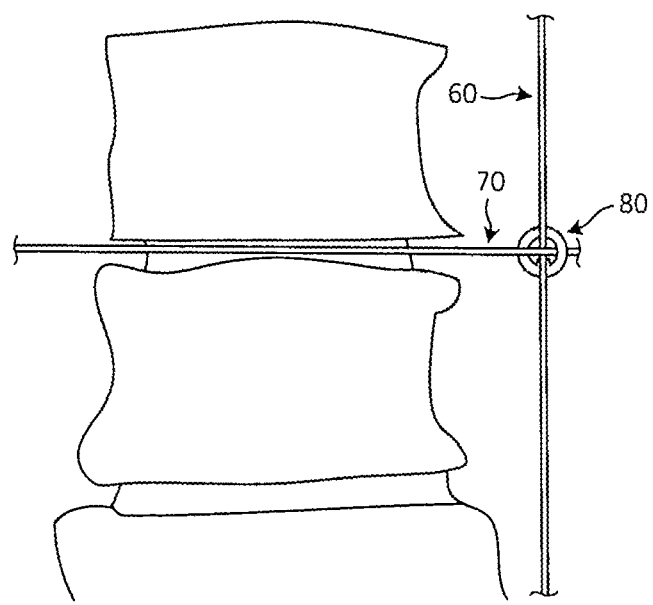
FIG. 7 is radiograph example of the technique of FIG. 7
Figure 8:
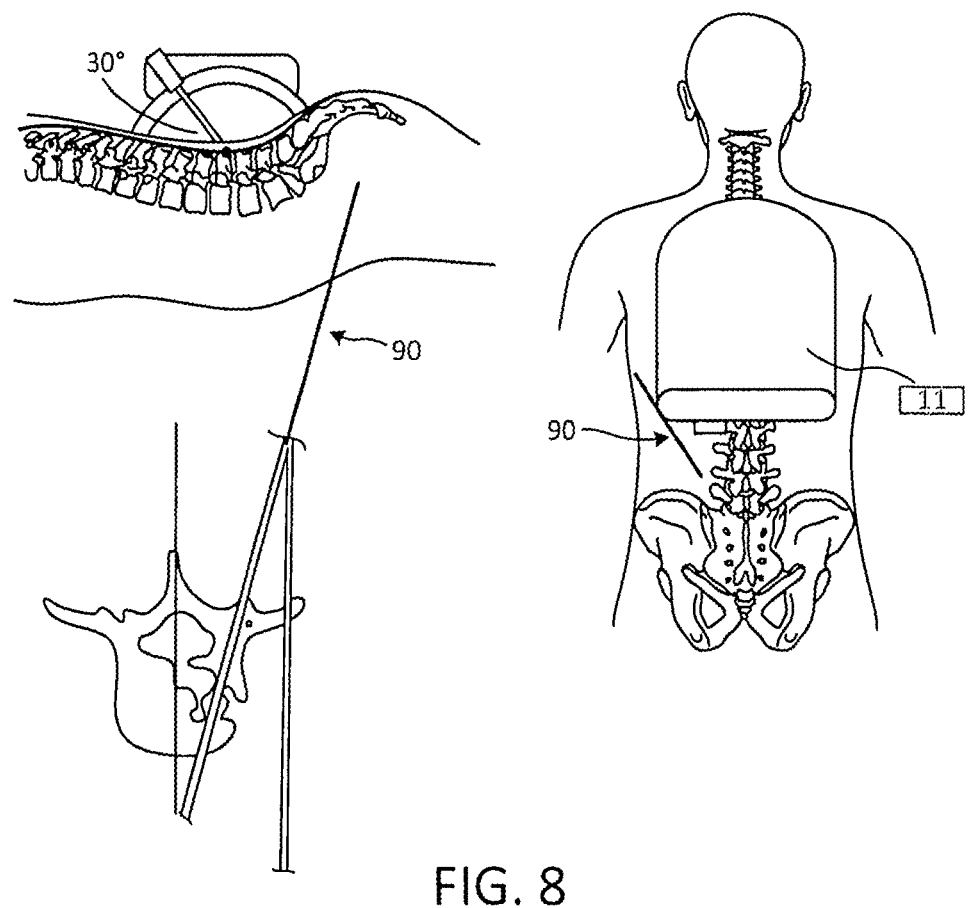
FIG. 8 is an illustration of final positioning of the guide pin.

The inclinometer guide pin 90 can now be deployed. Using both laser beam 60 and laser beam 70 as reference lines on the skin, the skin port or entry point 80 is established as illustrated in FIG. 7. Next, the inclinometer guide pin is positioned into the target holder and with the aid of the positioning arm positioned at pre-established angle in AP and target guide holder ML centerline brought into alignment with lateral laser light beam. In the example of FIG. 8, the angles are shown as 30 degrees lateral, 15 degrees A/P. Then the inclinometer guide pin is replaced with the procedural guide pin then advanced to its fully inserted position as shown in FIG. 8. Once the guide pin is successfully inserted, the procedure can begin.

Figure 9:
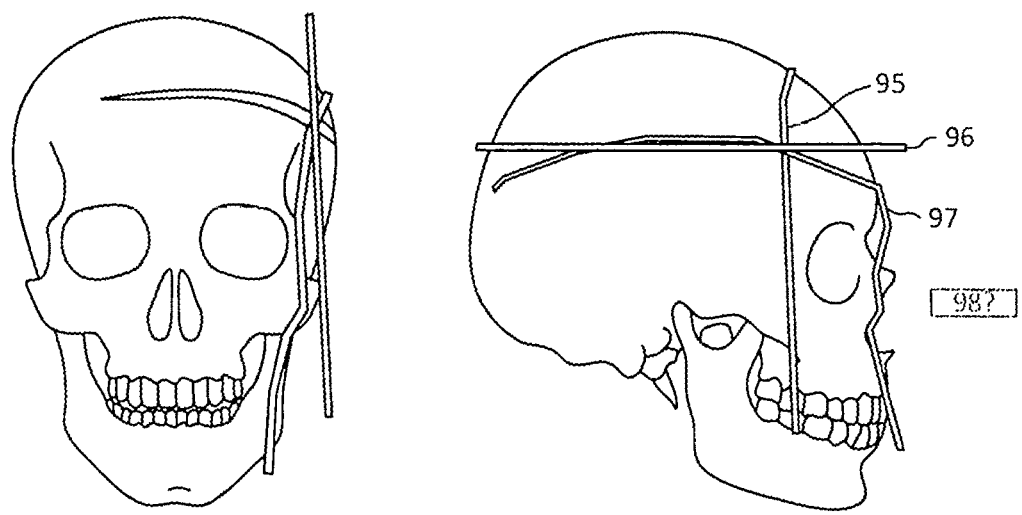
FIG. 9 is an illustration of the lateral and posterior views of the cranium, externally positioned in the posterior view and the intended trajectory of a surgical instrument through the skull in the lateral view. Straight vertical and horizontal lines illustrate radiopaque markers and contoured lines illustrate skin incision trajectories.

FIG. 9 is an illustration of the lateral and posterior views of the cranium, externally positioned in the posterior view and the intended trajectory of a surgical instrument through the skull in the lateral view. Straight vertical 95 and horizontal 96 lines illustrate radiopaque markers and contoured lines 97 and 98 illustrate skin incision trajectories.

Figure 10:
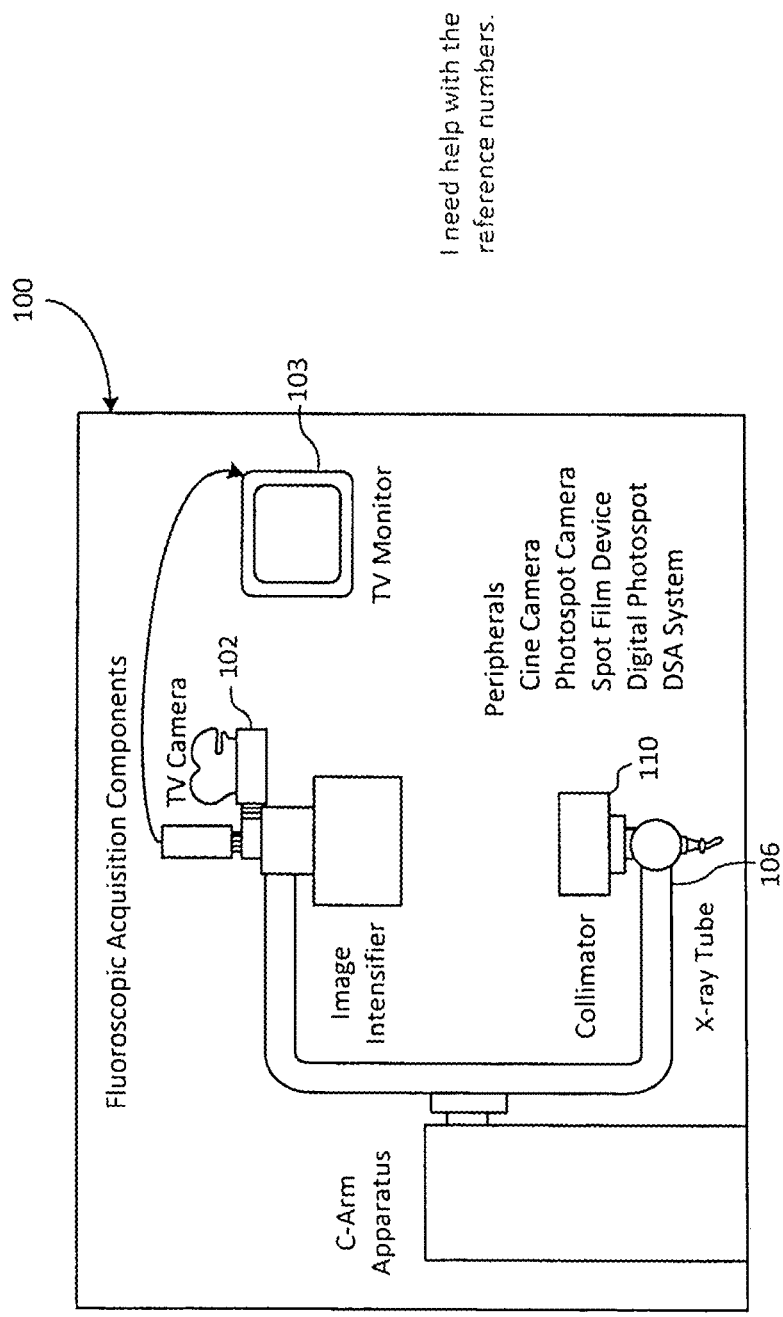
FIG. 10 is an illustration of a Fluoroscopic system in a side view.

FIG. 10 shows a representation of the side of view of a fluoroscope system 100 having an image intensifier 101, a CCD camera 102, a monitor 103, a C-Arm 104, a collimator 105 and an X-ray tube 106. The fluoroscope system 100 is known as a C-Arm system. The directed x-ray radiation generated by the X-ray tube 106 passes through the body part at position between the collimator 105 and the image intensifier 101 that is transmitted via the CCD camera 102 to the monitor 103. The X-rays are either continuous or pulsing so that the surgeon can view the surgery via the monitor 103 in real time.

Figure 11A:
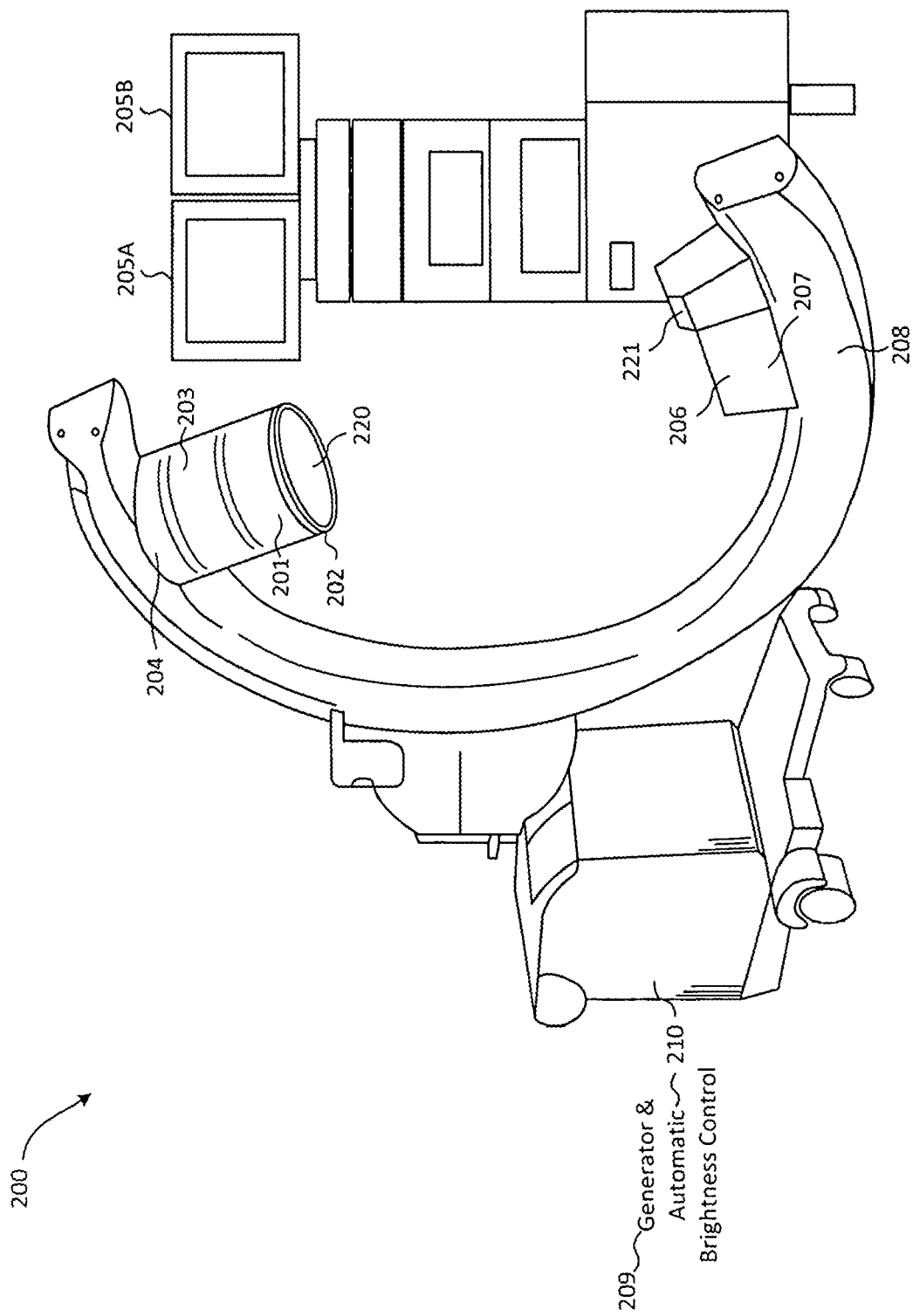
FIG. 11A is a perspective view of a Fluoroscopic C-Arm System.
Figure 11B:
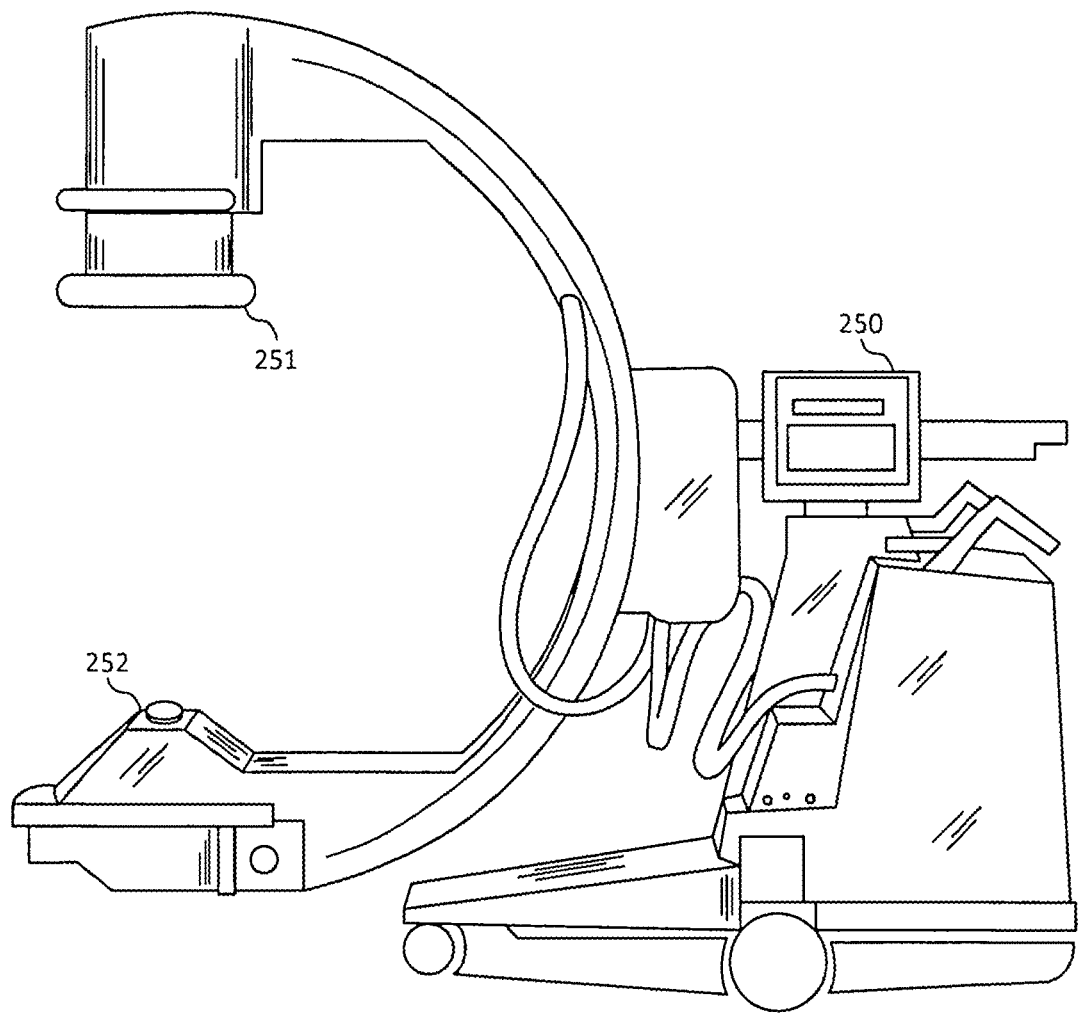
FIG. 11B is a side view of a GE Fluoroscopic C-Arm System.

FIG. 11A is a more detailed prospective view of a self-contained C-Arm Fluoroscopic system 200. The system 200 having an image intensifier 201, a grid 201, optics 203, a CCD camera 2014, monitors 205A and 205B, collimators 206, filters 207, X-ray tube 208, a generator 209 and automatic brightness control 210. The collar system 2 of FIG. 1 would fit around the circumference of the image intensifier 201 at 221 or around the Collimators 206 at 221. FIG. 11B is a side view of a version 250 of the Smart Laser Aimer from GE OEC (GE Healthcare, Salt Lake City, Utah) noted earlier is one of the systems to be used with the invention where is shows the position of the collar system 2 in FIG. 1 can be placed at positions 251 and 252, depending on the position of the physician and the need entry point for surgery.

Figure 12:
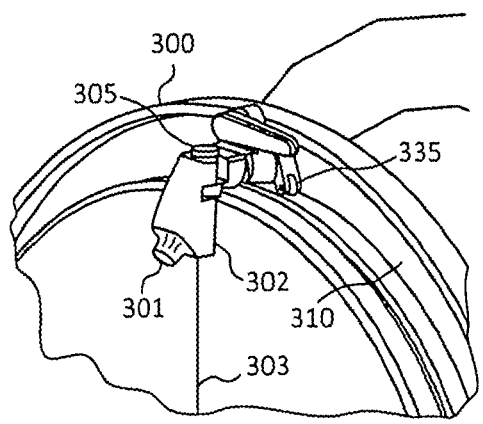
FIG. 12 is a perspective view of the collar for the image intensifier with the light source and the radiopaque marker.
Figure 13:
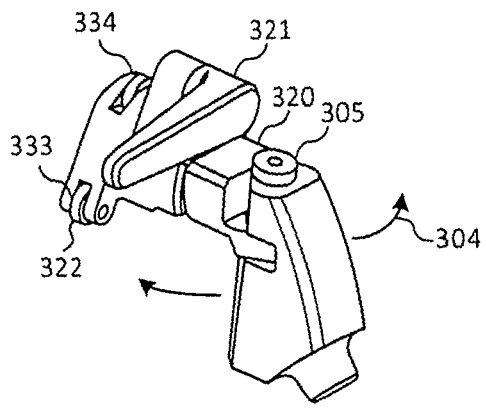
FIG. 13 is a perspective view of the light source and radiopaque marker and how the light source and holder have movement laterally.

The collar system 2 discussed in FIG. 1 would fit around the circumference image intensifier 101 in FIG. 10 or the Collimator 110. FIG. 12 shows in a perspective cut away the collar system 300 with light source 301, which in this instance is a laser light source, a radiopaque marker 302 that is held in housing 303 and secured in the housing by fitting 305. The housing 303 is part of an assembly 320, shown more clearly in FIG. 13. FIG. 13 illustrates that the housing 303 has pivoting movement 304 in an arc of no more than plus or minus 5 degrees. Limiting the radiopaque bar/visible light marker to pivot on its axis to −+5° insures projected lines under fluoroscopy stay within the limits of beam divergence parameters for accuracy of visible light on patient's skin. The radiopaque markers are always facing the center of the collar to minimize beam divergence. The entire assembly 320 fits into the circumferential channel 310 in FIG. 12. The entire assembly rotates around the circumference of the image intensifier of FIGS. 10 and 11 in the channel 310. The assembly has three wheels 333 and 334 in FIG. 13 and 335 in FIG. 12 that permit circumferential movement around channel 310. When the proper location is found by viewing the radiopaque marker 302 as it appears on monitor 103 in FIG. 10 or Monitor 205A.

The assembly 320 has a locking lever 321 that locks the assembly 320 in the desired circumferential position in channel 310 around the circumference of the image intensifier 101 in FIG. 10. The collar system 300 also fits around the circumference of the grid 202 and the assembly 320 would move around the circumference of the image intensifier 201 and the grid 201.

Figure 14:
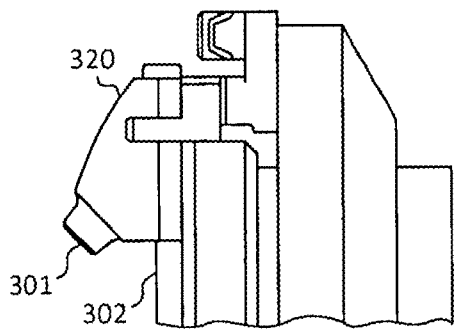
FIG. 14 is a side view of the collar for the image intensifier with the light source and radiopaque marker.
Figure 15:
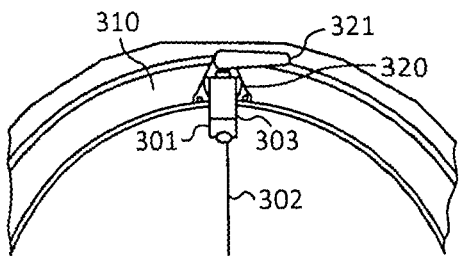
FIG. 15 is a front view of the collar for the image intensifier with the light source and radiopaque marker.
Figure 16:
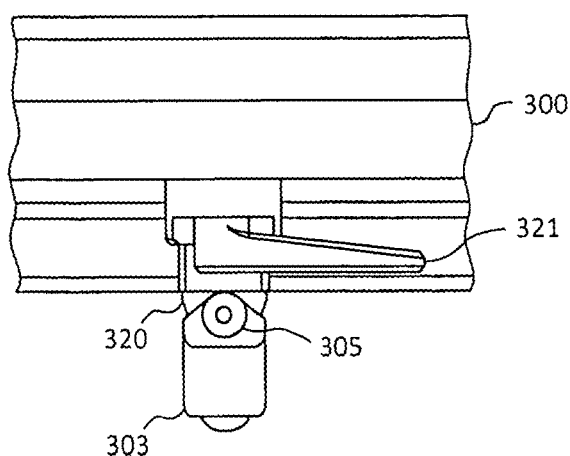
FIG. 16 is a top view of the collar for the image intensifier with the light source and radiopaque marker.

FIG. 14 a partial side view of the collar system with assembly 320 in channel 310 with the assembly having light source 310 and radiopaque 302 held in housing 303. FIG. 15 shows a partial front view of the collar system 300 showing channel 310, lock lever 321, housing 303 light source 301, and radiopaque marker 302. FIG. 16 shows a partial top view of collar system 300 and the assembly 320 with housing 303, fitting 305 and locking lever 321.

Figure 17:
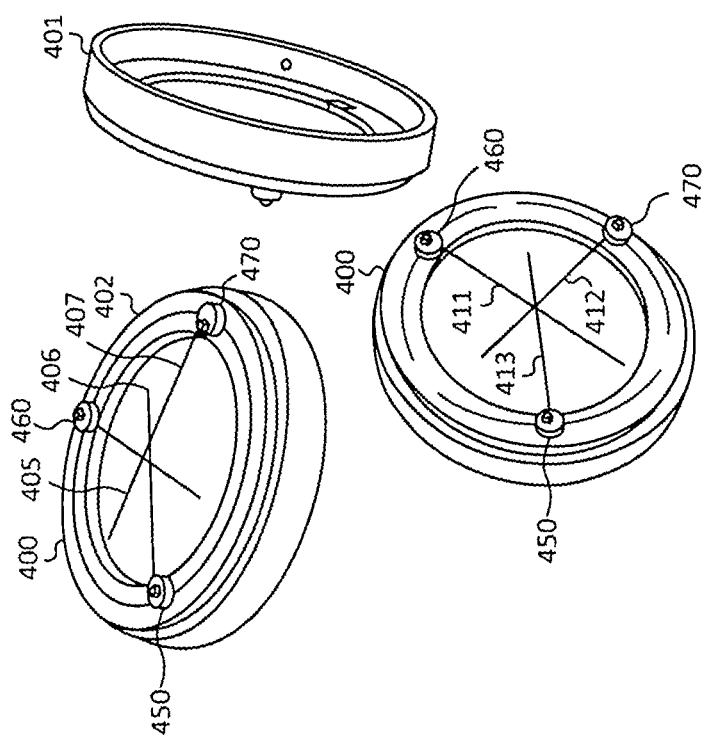
FIG. 17 shows perspective views of an alternative the collar for the image intensifier where the face rotates around the image intensifier.

FIG. 17 illustrates a perspective view of collar system 400 having collar 401 that fits around the circumference of the image intensifier 101 or the Collimator 110 in FIG. 10 and around the circumference 202 at 220 or the Collimators 206 at 221 of FIG. 11. There is outer rim 402 where the assemblies 440, 450, and 460 rotate circumferentially around the grid 202 or the image intensifier 101 or the Collimator 110. There are also assemblies 450, 460, and 470 that have radiopaque markers 405, 406, and 407, as well as lights sources 411, 412, and 413, which illustrates that there can be alternative collar systems with multiple light sources and multiple radiopaque markers. Limiting the radiopaque bar/visible light marker to pivot on its axis to −+5° insures projected lines under fluoroscopy stay within the limits of beam divergence parameters for accuracy of visible light on patient's skin. Also, the radiopaque markers are always facing the center of the collar to minimize beam divergence. With the introduction of square faces for the image intensifier or the collimator, the collar here can be easily constructed so that it was square to match up and have a circular channel and face to permitted the assemblies including the radiopaque markers and the light sources to travel around the circumference as shown. Further, with two assemblies on the collar system, the light sources can be arranged to create a target "x" by the intersection of the two light sources to create an entry point for medical instruments. Also, the two radiopaque markers may also be positioned to permit a target "x" on that can be followed by the surgeon.

Figure 18:
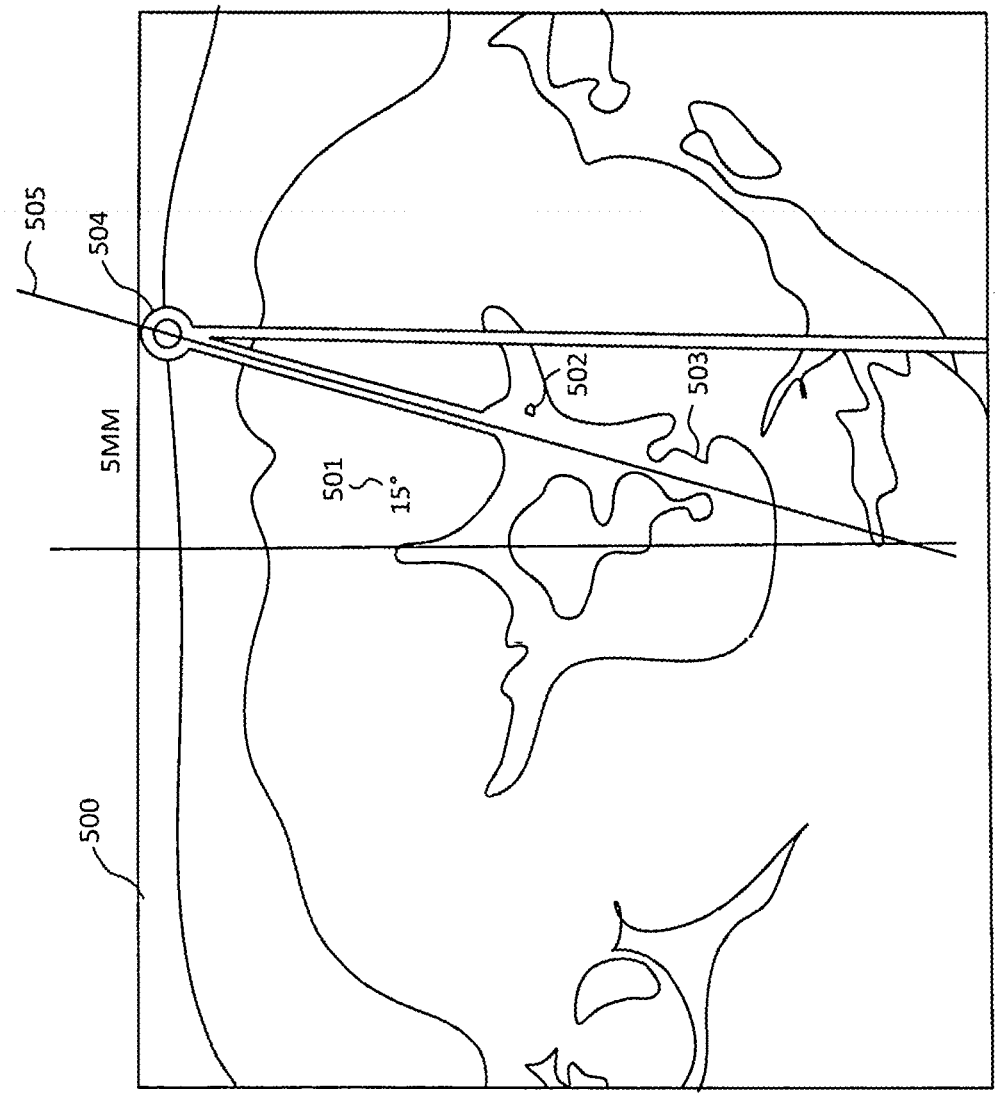
FIG. 18 is illustrative of the pre-surgical preparation.

FIG. 18 illustrates the use of preoperative preparation where starting with a CT or MRI axial slice of the affected area, you can plot your angles such as the 15-degree angle 501 and identify landmarks such as 502 and 503 and where the skin port 504 for entry of the guide pin that will mimic the radiopaque position 505. This will normally be accomplished preoperatively, but can also be accomplished intraoperatively as needed.

Figure 19:
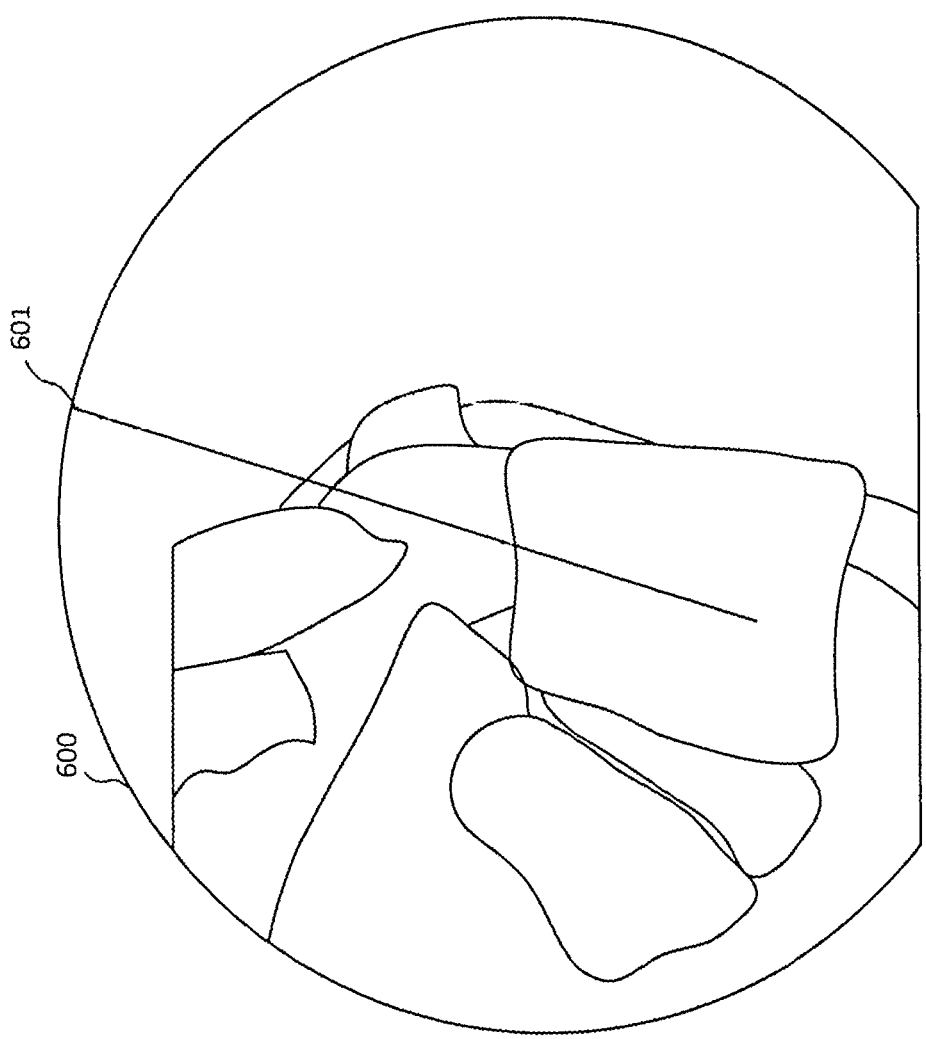
FIG. 19 illustrates the view from the monitor of the fluoroscope of the of the radiopaque marker.

FIG. 19 shows a lateral image 600 having a radiopaque marker 601. The added accuracy is to have the guide pin insertion (not shown) to mimic or be position the same as the radiopaque marker 601 to provide a more accurate and quicker insertion by also using the AP angle or azimuth angle of 15 degrees. The radiopaque marker provides the surgeon with an insertion to replicate here for use in spine surgery or in any other type of surgery where precision and accuracy are required and the desire is to accomplish the same as minimally invasive.

Figure 20:
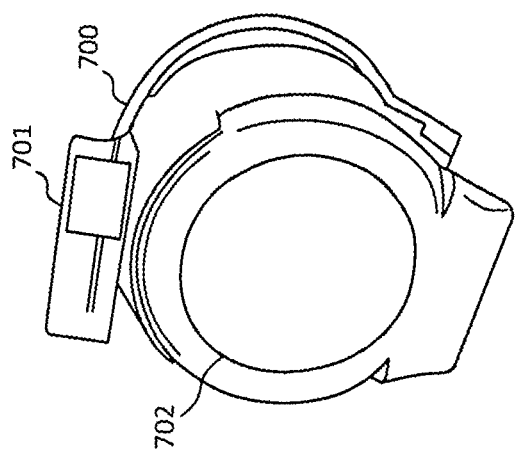
FIG. 20 illustrates an alternative collar for the image intensifier.

FIG. 20 illustrates another version of a collar system for the fluoroscopic system 700, where the position of the radiopaque marker 702 is projected on image 600 which would be found on monitor 103 of Fluoroscopic system 100 in FIG. 10 or on monitor 205A on fluoroscopic system in FIG. 11. The surgeon now has the image that she can precisely follow in inserting a guide pin.

Figure 21A:
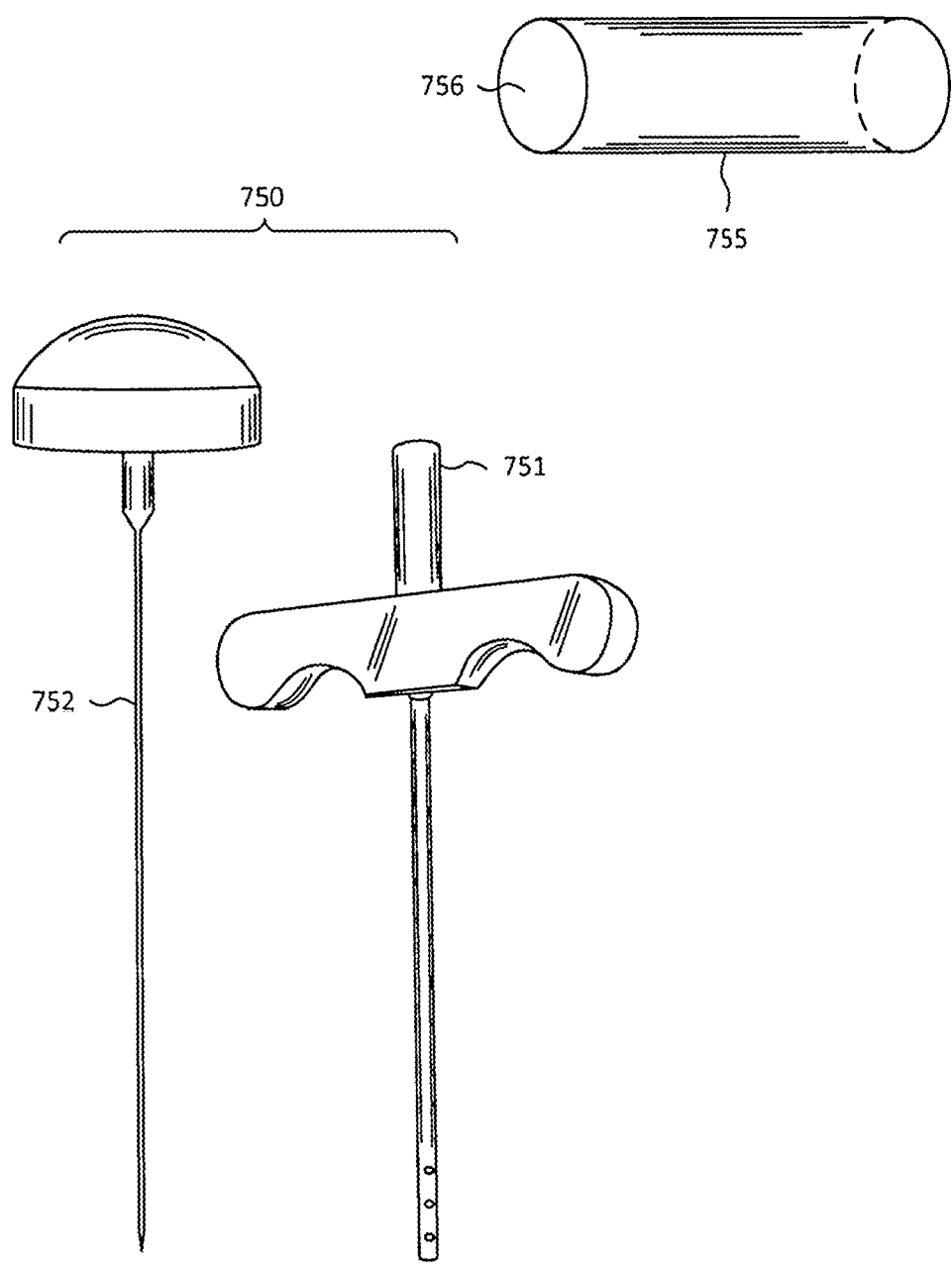
FIG. 21A illustrates a Jamshidi, a stylet and a target guide holder.
Figure 21B:
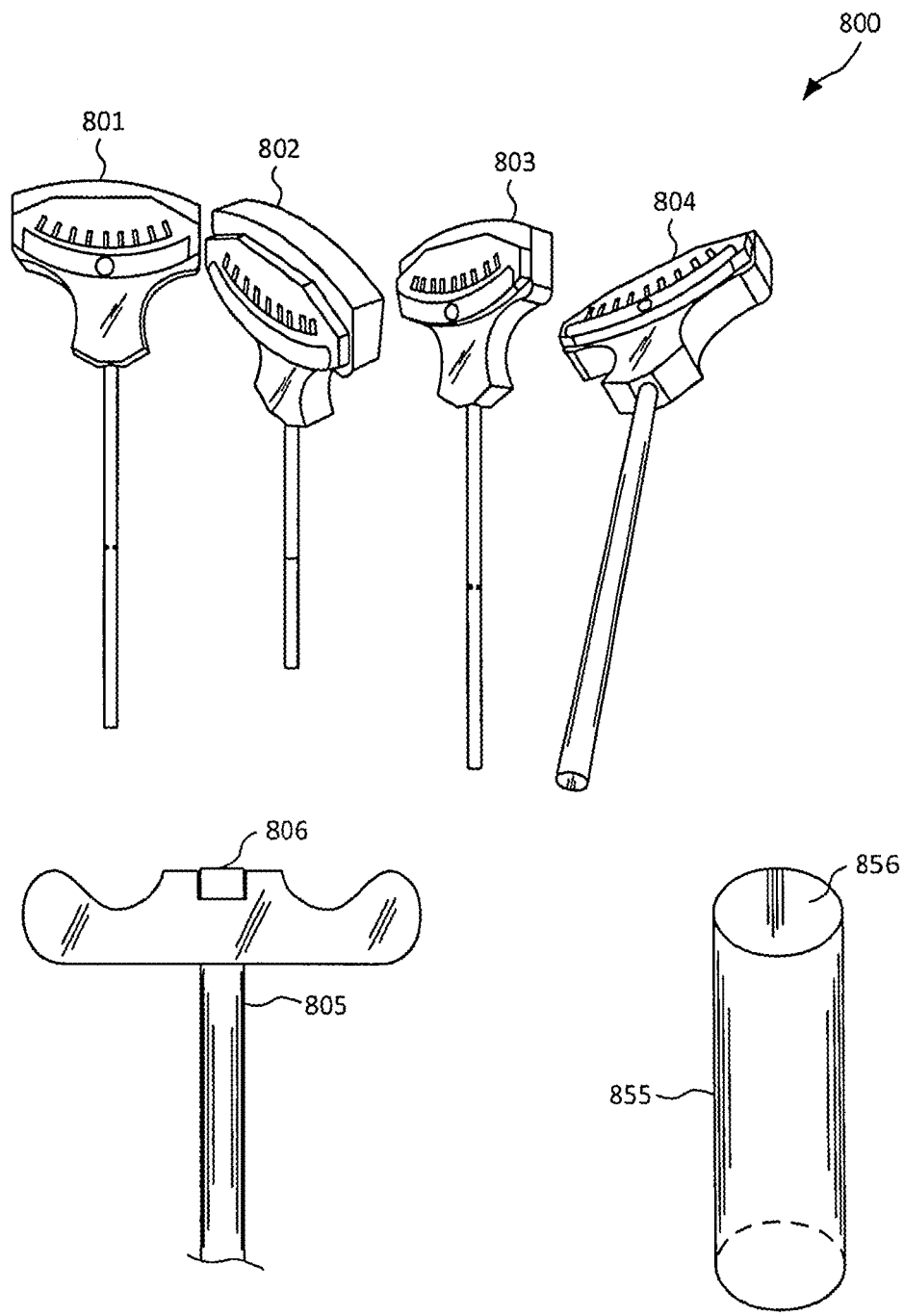
FIG. 21B illustrates an inclinometer for determine the AP angle and the lateral angle.

FIG. 21A illustrates a Jamshidi 750 with stylet 752 and cannula 751 where the stylet slides into to complete the Jamshidi. Also, illustrated in FIG. 21A is target guide holder 755 with an opening that goes completely through the center of 755. The target guide holder is made of a plastic that cannot be picked up by the X-rays of the fluoroscopic systems. The target guide 755 is held by a standard mechanical arm used in surgery so that it can be properly positioned by the position of the radiopaque marker and the angle in the AP Plane and the Angles in the ML plane for proper insertion of the surgical instruments. FIG. 21B illustrates a series of bubble inclinometers 800 in various positions for inclinometers 801, 802, 803, and 804. These inclinometers will slide into the Jamshidi cannula 805 through opening 806 or the inclinometers can slide into the target guide holder 855 through opening 856 that goes through the entire length of the target guide holder 855 in order to determine the angel for the lateral plane and the AP plane for use correct angle and placement of the instruments such as a Jamshidi to make the initial incision.

FIG. 21A illustrates a Jamshidi 750 that can be placed in a target guide holder 755. The holder would be held by a standard mechanical arm used in surgery (not shown) that would not be picked up on the x-ray of the fluoroscope system, whether they be system illustrated in FIG. 10, 11A or 11B or any other commercial fluoroscopic system. FIG. 21 B illustrates bubble inclinometers 800 that would be used to provide the correct angle of the Jamshidi. The stylet of Jamshidi 751 would be withdrawn and an inclinometer such as 801 can be used by placing in the cannula of the Jamshidi 751 or 806 of 805 in FIG. 21B and the angle positioning can be determined for the AP Plane and the ML plane. Finally, the position of the Jamshidi 750 in target guide holder 755 would be aligned to mimic the position of the radiopaque marker 601 in FIG. 19. Then the surgeon can position the mechanical arm over the point of intersection of the entry point 51 of FIG. 4, which is where the two light sources intersect. Once there is the final position at point 51, the surgeon can then make the incision using the Jamshidi 750. The surgeon can also use a trocar, cannula, a drill bit or any surgical device used to make an incision at point 51 in FIG. 4. The instant invention and its many uses should not be limited to spine surgery, but can be used in surgery where there are two planes or even where there is a single plane of interest.

Figure 22:
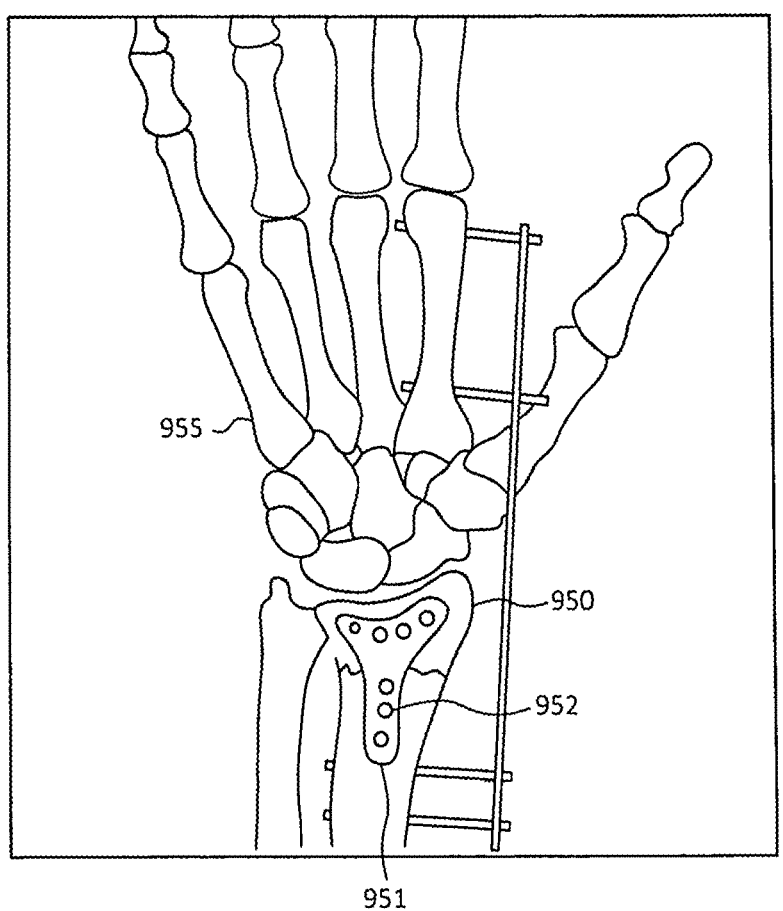
FIG. 22 illustrates a hand and wrist having a plate with screws.

FIG. 22 is an illustration of a wrist 950 having a plate 951 and screws 952 with hand 955 that can benefit from the precision of the instant invention. Horizontal and vertical laser lines can be projected on the plane of the screw holes in the x and y plane and a radiopaque marker can be used to establish the correct position for inserting the screws 952.

Figure 23:
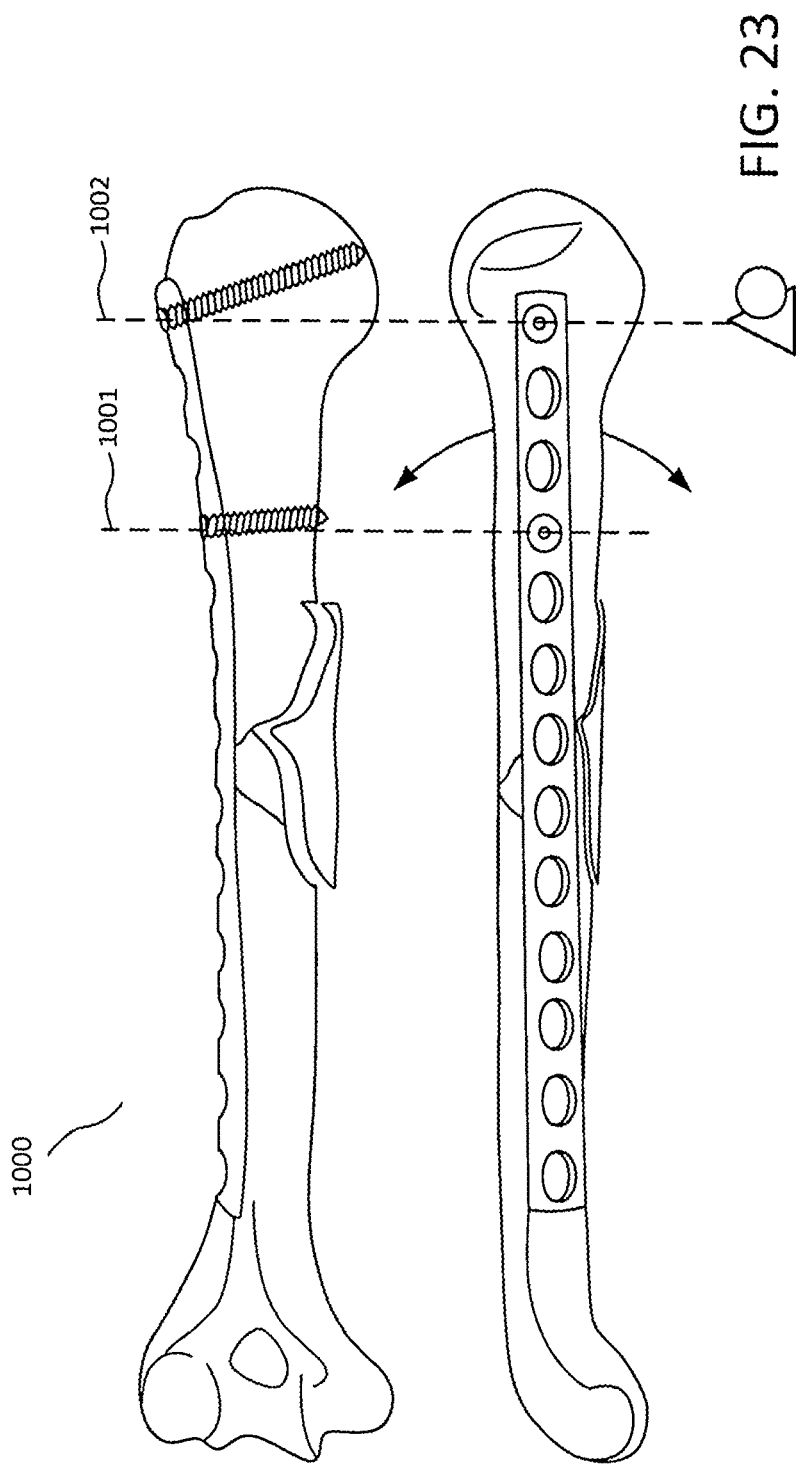
FIG. 23 illustrates a Humeral Shaft with a plate and screws.

FIG. 23 is an illustration of a Humeral Shaft 1000 that can benefit from the instant invention as the screw lines 1001 and 1002 can be projected on the skin from the laser light sources, as well as the radiopaque marker, not shown, can illustrate further an exact duplication of the insert points for the screws.

Figure 24:
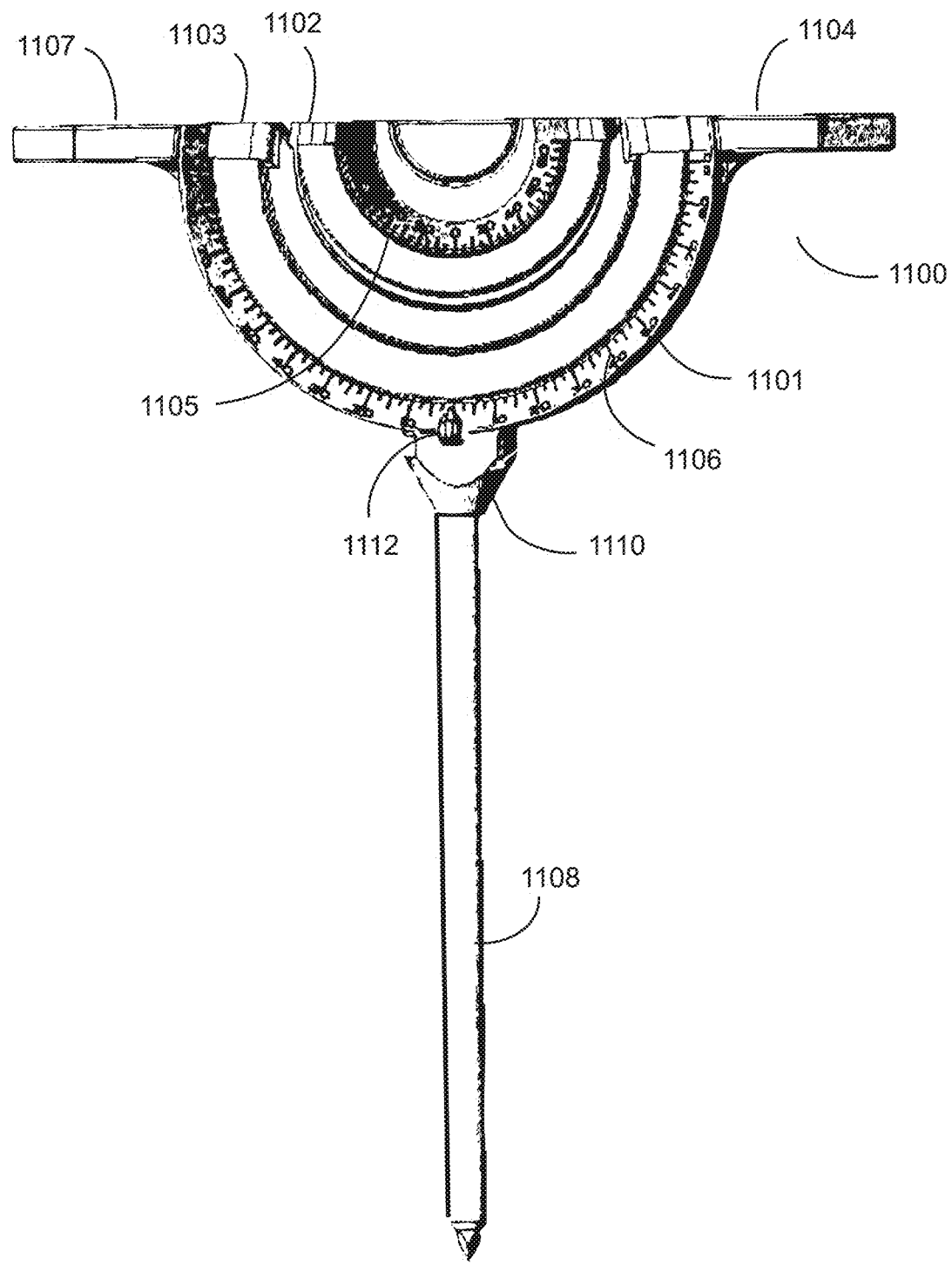
FIG. 24 is an illustration of taking the Jamshidi of FIGS. 21 and 21A with further improvements and modifications.

FIG. 24 is an illustration of a device which combines features of the Jamshidi of FIGS. 21A and 21B with further improvements and modifications. The instrument FIG. 24, will be referred to as a an instrument-guiding device 1100. Instrument-guiding device 1100 has a body 1101 having first inclinometer 1102 for measuring an angle in one plane and a second inclinometer 1103 for measuring an angle in another plane. The planes can be, for example, the lateral plane, and the anterior-posterior (AP) plane at 90 degrees from the lateral plane. The body 1101 has a flange at each side thereof, which can be referred to as first flange 1104 and second flange 1107. First inclinometer 1102 has angle indicia 1105 and second inclinometer 1103 has angle indicia 1106 each for establishing an angle relative to a position of the instrument-guiding device in different planes in order to assist in determining the skin-entry point for the entry incision for and placement of a surgical instrument such as a pedicle screw, a cannula, a Steinman pin, a Moore's Pin, a Knowel's Pin, a Denham Pin. K Wire, or any such similar surgical instrument.

Also illustrated in FIG. 24, there is a cannula 1108 connected to the body 1101 at fitting 1110. The fitting 1110 can be a screw, snap in device or any component that connects a cannula 1108 to the body 1101. The cannula 1108 can in the alternative be a needle, a Steinman pin, a Moore's Pin, a Knowel's Pin, a Denham Pin, K Wire, a Star Wrench or any surgical instrument that would assist in any orthopedic surgery with the use of the instrument-guiding device. FIG. 24 also illustrates angle indicator 1112 that can travel around the edge of the indicia 1106.

Figure 25:
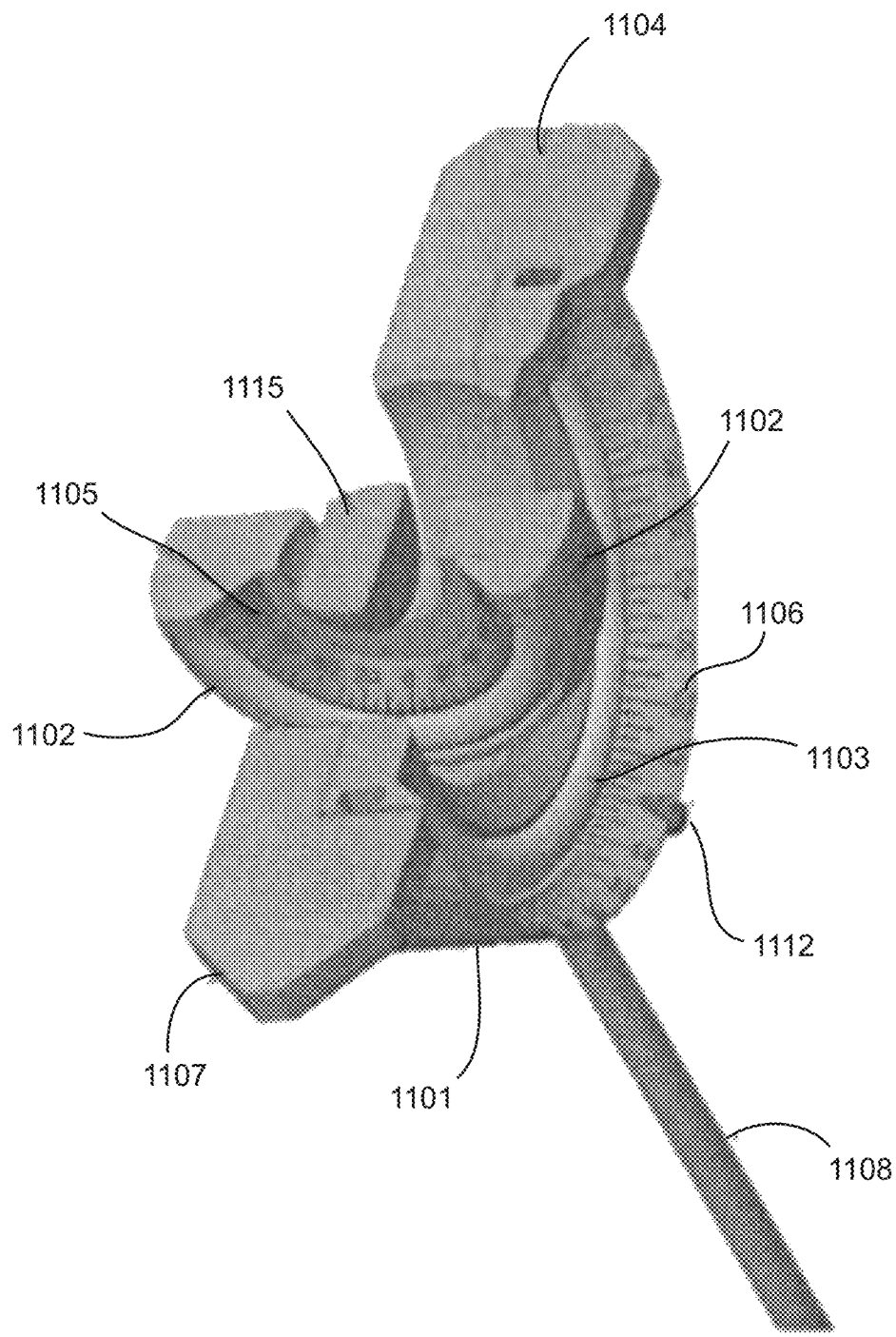
FIG. 25 illustrates a perspective view from the top of the Spotter.

FIG. 25 illustrates a perspective view from the top of the instrument-guiding device 1100. It illustrates that first inclinometer 1102 rotated 90 degrees from second inclinometer 1103. This is to enable the use of the instrument-guiding device 1100 to find the correct incision angle in each of two planes. The instrument-guiding device 1100 has impact surface 1115 that can be used to push the cannula or needle 1108 into appropriate position during orthopedic surgery to create an incision.

Figure 26:
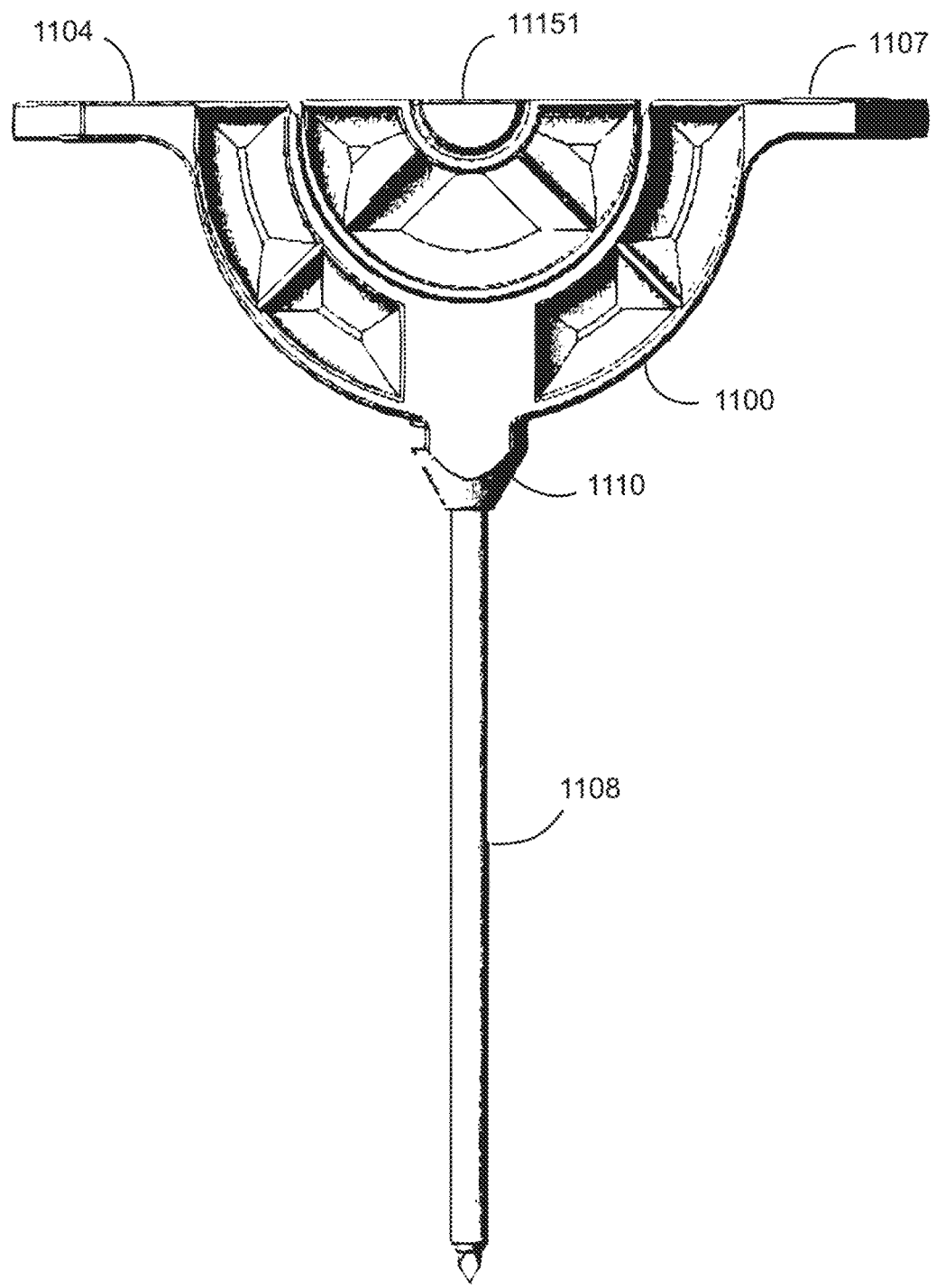
FIG. 26 is a back view of the spotter having the Spotter body, connector, needle or cannula, flange surfaces and impact surface, which can be impacted using one hands or other instruments, such as a hammer like device.

FIG. 26 is a rear view of the instrument-guiding device 1100 having the body 1101, connector 110, needle or cannula 108, first and second flange surfaces 1104 and 1107, and impact surface 1115, which can be impacted using one hands or other instruments, such as a hammer like device, which is not shown.

FIG. 27 illustrates the Spotter Body 1101 ready to receive a needle, cannula, pin or start wrench at connector 1110 or any similar such device for use during orthopedic surgery.

FIG. 28 illustrates an alternative Spotter 1200, which has a Spotter body 1201, bubble vane 1202, bubble vane 1203 with angle indicia 1205 and 1206, impact surface 1215, Flanges 1204 and 1207 and graduated marked needle or cannula 1208 connected at connector 1210, which can be a screw, snap-on or any easy manner to connect the cannula 1208. Again 1208, can be a cannula, a needle, a Steinman pin, a Moore's Pin, a Knowel's Pin, a Denham Pin, K Wire, a Star Wrench or any device that would assist in any orthopedic surgery with the use of the Spotter 1200. There is also the angle marker 1212 that rides along the curved surface of the indicia 1206 indicating the angle of bubble vane 1203. The impact surface 1215 is more substantial in this 1200 version of the Spotter than the 110 version of the Spotter above and can be seen in the side view of the Spotter 1200 in FIG. 29.

FIG. 30 illustrates a bottom view of both Spotter 1100 and 1200 illustrating the Spotter Body 1201, the connector 1210, the angle indicator 1212 and indicia surface 1206.

The use of the Spotters detailed herein provide a great advance over the use of K Wire for screw insertion because K Wire can break, bend, pull out or advance during the orthopedic procedure.

The method and system here can be used not just for surgery but also for training of surgeons on cadavers or simulated bodies to improve technique and understanding. The training aspect of the instant invention is a key use of the method and system disclosed herein because it will provide a much more precise and accurate surgical technique being developed by surgeons.

Of course, the foregoing description is that of certain features, aspects and advantages of the present invention, to which various changes and modifications can be made without departing from the spirit and scope of the present invention.

Moreover, the surgical targeting systems and methods need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed surgical marking systems and methods.

I claim:

1. A system comprising:
   a surgical instrument, and
   an instrument-guiding device, the instrument-guiding device including:

a body extending between a first flange and a second flange, a first gravimetric inclinometer integrated with the body between the first flange and the second flange and configured for measuring an angle with respect to alignment of the surgical instrument in a first plane, a second gravimetric inclinometer for measuring an angle with respect to alignment of the surgical instrument in a second plane, wherein the second plane is distinct from the first plane, and an opening extending through each of the body and the first and second gravimetric inclinometers;

wherein the body is configured to removably engage the surgical instrument at the opening.

2. A system for guiding a surgical instrument during a medical procedure, the system comprising:

a collar device, and an instrument-guiding device configured for use with the collar device;

the instrument-guiding device comprising:

a body extending between a first flange and a second flange, a gravimetric inclinometer being integrated with the body and configured to measure a first angle indicating alignment of the instrument-guiding device in a first plane, the body being configured to couple with the surgical instrument; and wherein the collar device comprises:

a radiopaque marker configured to be aligned with an anatomical feature associated with the medical procedure, and a laser light source configured to emit laser light for replicating a plane extending through each of the radiopaque marker and the anatomical feature;

wherein the system is configured to guide the surgical instrument with the instrument-guiding device being aligned with the laser light of the collar device, and the gravimetric inclinometer being maintained at the first angle.

3. The system of claim 2, wherein the surgical instrument is selected from the group consisting of: a pedicle screw, cannula, Steinman pin, Moore pin, Knowles pin, Denham pin, and Kirschner wire.

* * * * *